(12) United States Patent
Flaherty et al.

(10) Patent No.: US 12,378,211 B2
(45) Date of Patent: Aug. 5, 2025

(54) CARBONIC ANHYDRASE INHIBITORS AND ANTIBIOTICS AGAINST MULTIDRUG RESISTANT BACTERIA

(71) Applicant: Purdue Research Foundation, West Lafayette, IN (US)

(72) Inventors: Daniel P Flaherty, West Lafayette, IN (US); Mohamed Seleem, West Lafayette, IN (US); Jatinder Kaur, Edmonton (CA); Xufeng Cao, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 952 days.

(21) Appl. No.: 17/415,899

(22) PCT Filed: Dec. 18, 2019

(86) PCT No.: PCT/US2019/067020
§ 371 (c)(1),
(2) Date: Jun. 18, 2021

(87) PCT Pub. No.: WO2020/131980
PCT Pub. Date: Jun. 25, 2020

(65) Prior Publication Data
US 2022/0056001 A1 Feb. 24, 2022

Related U.S. Application Data

(60) Provisional application No. 62/781,824, filed on Dec. 19, 2018.

(51) Int. Cl.
*C07D 285/135* (2006.01)
*A61P 31/04* (2006.01)

(52) U.S. Cl.
CPC .......... *C07D 285/135* (2013.01); *A61P 31/04* (2018.01)

(58) Field of Classification Search
CPC ............................. C07D 285/135; A61P 31/04
USPC ....................................................... 514/363
See application file for complete search history.

(56) References Cited

U.S. PATENT DOCUMENTS

| | | | |
|---|---|---|---|
| 2004/0204493 A1* | 10/2004 | Scott | A61K 31/433 514/602 |
| 2009/0175794 A1 | 7/2009 | Zimmerman et al. | |
| 2018/0236000 A1 | 8/2018 | Dunman | |
| 2018/0263982 A1 | 9/2018 | Siracusa | |

FOREIGN PATENT DOCUMENTS

WO    2017161195    9/2017

OTHER PUBLICATIONS

Capasso, C. et al., "An Overview of the Selectivity and Efficiency of the Bacterial Carbonic Anhydrase Inhibitors," Current Medicinal Chemistry, (2015), 22, (pp. 2130-2139).
Faith, HE., "2-Amino-5-thiazolesulfonic Acid Derivatives," Downloaded via Purdue University on Sep. 27, 2023, (1 page).
Maren, T.H. et al., "The Transcorneal Permeability of Sulfonamide Carbonic Anhydrase Inhibitors and Their Effect on Aqueous Humor Secretion," Exp. Eye Res. (1983), 36, (pp. 457-480).
Masereel, B. et al., "Carbonic Anhydrase Inhibitors: Anticonvulsant Sulfonamides Incorporating Valproyl and Other Lipophilic Moieties," J. Med. Chem. (2002), 45, (pp. 312-320).
Ohkusa, T. et al., "The Role of Bacterial Infection in the Pathogenesis of Inflammatory Bowel Disease," Internal Medicine, vol. 43, No. 7, (2004) (pp. 534-539).
PubChem CID 394898, Create Date: Mar. 26, 2005, pp. 1-13, p. 2.
PubChem CID 519309, Create Date: Mar. 27, 2005, pp. 1-14, p. 2.
PubChem CID 10515762, Create Date: Oct. 25, 2005, pp. 1-11, p. 2.
PubChem Cid 20475140, Create Date: Dec. 5, 2007, pp. 1-13, p. 2.
Supuran, C.T., "Bacterial Carbonic Anhydrases as Drug Targets: Toward Novel Antibiotics?" www.frontiershin.org., Article 34, vol. 2, (2011) (pp. 1-6).
Supuran C.T., "Carbonic Anhydrases: Novel Therapeutic Applications for Inhibitors and Activators," Nature Publishing Group, vol. 7, (2008), (pp. 168-181).
Turkmen, H. et al., "Carbonic Anhydrase Inhibitors. Novel Sulfanilamide/Acetazolamide Derivatives Obtained by the Tail Approach and their Interaction with the Cytosolic Isozymes I and II, and the Tumor-Associated Isozyme IX," Bioorganic & Medicinal Chemistry Letters, 15, (2005) (pp. 367-372).
Vaughan, J.R. et al., "Heterocyclic Sulfonamides as Carbonic Anhydrase Inhibitors. 2-Acylamido- and 2-Sulfonamido-I,3,4-thiadiazole-5-Sulfonamides," Notes, vol. 21,(1956), (pp. 700-701).
Younis, W et al., "In Vitro Screening of an FDA-Approved Library Against ESKAPE Pathogens," Current Pharmaceutical Design, (2017), 23, (pp. 2147-2157).
International Search Report for International Application No. PCT/US19/67020, dated Feb. 19, 2020. (4 pages).

\* cited by examiner

*Primary Examiner* — Kristin A Vajda
(74) *Attorney, Agent, or Firm* — Purdue Research Foundation

(57) ABSTRACT

The invention described herein generally relates to novel therapeutic compounds, and in particular to carbonic anhydrase inhibitors as a narrow spectrum antibiotics against drug resistant bacteria and methods for treating those infection diseases in mammals using the described carbonic anhydrase inhibitors or a pharmaceutical formulation thereof.

12 Claims, 5 Drawing Sheets

CARBONIC ANHYDRASE INHIBITORS AND ANTIBIOTICS AGAINST MULTIDRUG RESISTANT BACTERIA

CROSS-REFERENCE TO RELATED APPLICATIONS

The present U.S. patent U.S. patent application is a national stage entry under 35 U.S.C. § 371 (b) of International Application No. PCT/US19/67020, filed on Dec. 18, 2019, which is related to and claims the priority benefits of U.S. Provisional Application Ser. No. 62/781,824, filed Dec. 19, 2018, the contents of which are hereby incorporated by reference in their entirety into the present disclosure.

TECHNICAL FIELD

The present disclosure generally relates to therapeutic compounds, and in particular to carbonic anhydrase inhibitors as a narrow spectrum antibiotics against multidrug resistant bacteria and methods for treating those infection diseases in mammals using the described carbonic anhydrase inhibitors or a pharmaceutical formulation thereof.

BACKGROUND

This section introduces aspects that may help facilitate a better understanding of the disclosure. Accordingly, these statements are to be read in this light and are not to be understood as admissions about what is or is not prior art.

Vancomycin-resistant enterococci (VRE) is the one of leading cause of drug-resistant hospital-acquired infections (HAIs) in the US, triggering the Centers for Disease Control and Prevention to classify VRE as a serious healthcare threat. VRE is responsible for more than 5% of all deaths attributed to an antibiotic-resistant infection in the USA. Despite the prevalence and severity of VRE infections, there are limited number of effective antibiotics available for treatment. Moreover, the drugs that are available are also harmful to the normal gut microbiota ultimately contributing the problematic cycle of microbial imbalance known as dysbiosis, which *enterococcus* takes advantage of in the first place (Arias and Murray, Nature 2012, 10, 266-278; van Harten, et al., Trends in Microbiol. 2017, 25 (6), 467-479; Beganovic, et al., Clinical Infectious Disease 2018, 67 (2), 303-309). The World Health Organization recently categorized VRE as one of 12 bacterial pathogens for which new therapeutics and alternative strategies are urgently needed. There are unmet needs for new and more effective treatments for infection diseases.

BRIEF DESCRIPTION OF DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein.

DETAILED DESCRIPTION

Figure 1:
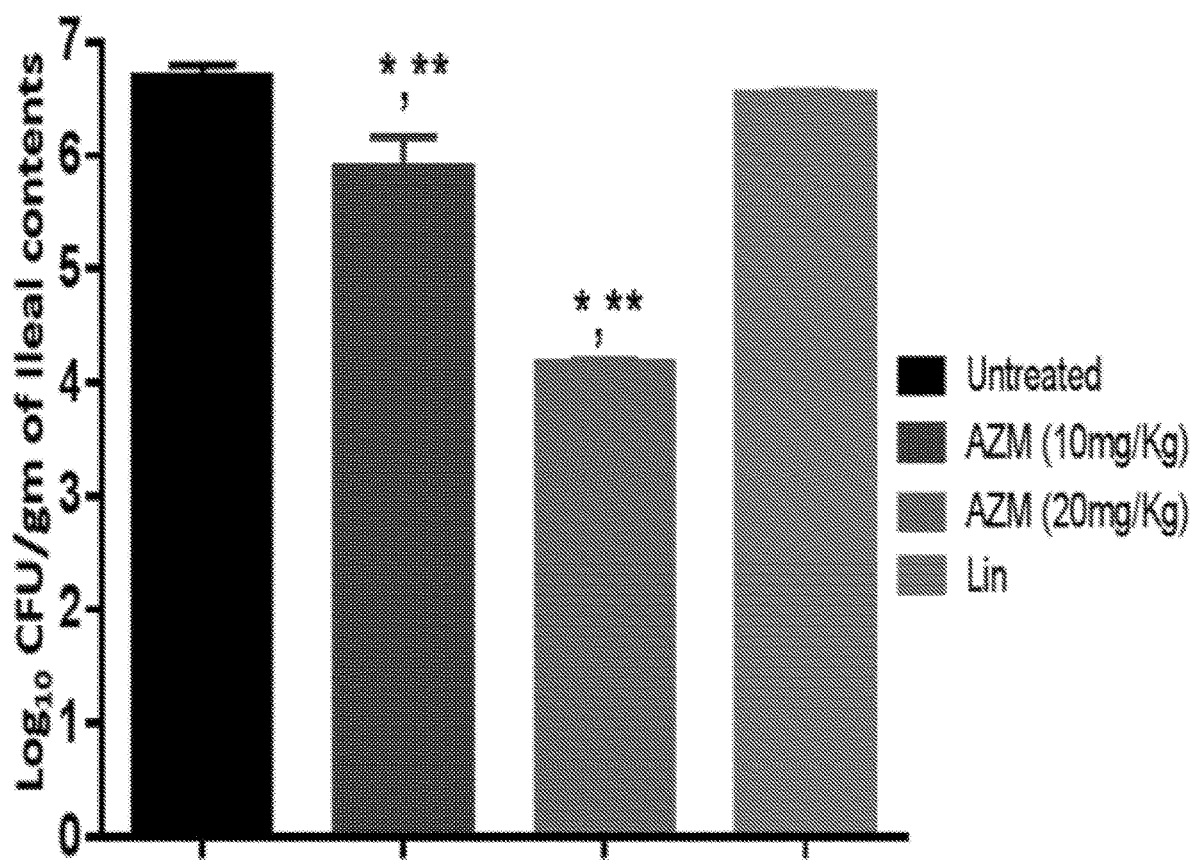
FIG. 1: VRE in ileal content of infected mice treated with Acetazolamide (10 and 20 mg/kg), linezolid (10 mg/kg) once daily for 8 days. (*) significant from control, (**) significant from linezolid.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Unless defined otherwise, all technical and scientific terms used herein have the same meaning as commonly understood to one of ordinary skill in the art. As defined herein, the following terms and phrases shall have the meanings set forth below.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, 99%, 99.5%, 99.9%, 99.99%, or at least about 99.999% or more of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

The term "alkyl" as used herein refers to substituted or unsubstituted straight chain and branched alkyl groups and cycloalkyl groups having from 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neo-pentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to substituted or unsubstituted straight chain and branched divalent alkenyl and cycloalkenyl groups having from 2 to 20 carbon atoms ($C_2$-$C_{20}$), 2 to 12 carbons ($C_2$-$C_{12}$), 2 to 8 carbon atoms ($C_2$-$C_8$) or, in some embodiments, from 2 to 4 carbon atoms ($C_2$-$C_4$) and at least one carbon-carbon double bond. Examples of straight chain alkenyl groups include those with from 2 to 8 carbon atoms such as —CH—CH—, —CH—CHCH$_2$—, and the like. Examples of branched alkenyl groups include, but are not limited to, —CH═C (CH$_3$)— and the like.

An alkynyl group is the fragment, containing an open point of attachment on a carbon atom that would form if a hydrogen atom bonded to a triply bonded carbon is removed from the molecule of an alkyne. The term "hydroxyalkyl" as used herein refers to alkyl groups as defined herein substituted with at least one hydroxyl (—OH) group.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to substituted or unsubstituted aromatic and non-aromatic ring compounds containing 3 or more ring members, of which, one or more is a heteroatom such as, but not limited to, B, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$).

A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclylalkyl groups include, but are not limited to, furan-2-yl methyl, furan-3-yl methyl, pyridine-3-yl methyl, tetrahydrofuran-2-yl methyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N (group) 3 wherein each group can independently be H or non-H, such as alkyl, aryl, and the like. Amines include but are not limited to R—$NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —$NH_2$, —NHR, —$NR_2$, —$NR_3^+$, wherein each R is independently selected, and protonated forms of each, except for-$NR_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, —$CF(CH_3)_2$ and the like.

The term "optionally substituted," or "optional substituents," as used herein, means that the groups in question are either unsubstituted or substituted with one or more of the substituents specified. When the groups in question are substituted with more than one substituent, the substituents may be the same or different. When using the terms "independently," "independently are," and "independently selected from" mean that the groups in question may be the same or different. Certain of the herein defined terms may occur more than once in the structure, and upon such occurrence each term shall be defined independently of the other.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

Further, in each of the foregoing and following embodiments, it is to be understood that the formulae include and represent not only all pharmaceutically acceptable salts of the compounds, but also include any and all hydrates and/or solvates of the compound formulae or salts thereof. It is to be appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non-crystalline and/or amorphous forms of the compounds.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

Illustrative formats for oral administration include tablets, capsules, elixirs, syrups, and the like. Illustrative routes for parenteral administration include intravenous, intraarterial, intraperitoneal, epidural, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the coadministered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 µg/kg to about 1 g/kg. The dosages may be single or divided, and may administered according to a wide variety of protocols, including q.d. (once a day), b.i.d. (twice a day), t.i.d. (three times a day), or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In addition to the illustrative dosages and dosing protocols described herein, it is to be understood that an effective amount of any one or a mixture of the compounds described herein can be determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The term "patient" includes human and non-human animals such as companion animals (dogs and cats and the like) and livestock animals. Livestock animals are animals raised for food production. The patient to be treated is preferably a mammal, in particular a human being.

In some illustrative embodiments, the invention is related to a method for treating a patient with a bacterial infection comprising the step of administrating therapeutically effective amount of a carbonic anhydrase inhibitor or a pharmaceutically acceptable salt thereof, together with one or more diluents, excipients or carriers, to the patient in need of treatment for said infection.

In some illustrative embodiments, the invention is related to a method for treating a patient with a bacterial infection comprising the step of administrating therapeutically effective amount of a carbonic anhydrase inhibitor or a pharmaceutically acceptable salt thereof, together with one or more diluents, excipients or carriers, to the patient in need of treatment for said infection, wherein said carbonic anhydrase inhibitor has the formula (I)

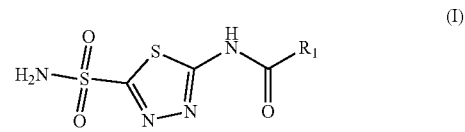

or a pharmaceutically acceptable salt thereof, wherein
R₁ is an alkyl, alkenyl, alkynyl, heteroalkyl, heteroalkenyl, heterocyclyl, cycloalkyl, cycloalkenyl, cycloheteroalkyl, cycloheteroalkenyl, alkylaryl, alkenylaryl, aryl, arylalkyl, and arylalkenyl, each of which is optionally substituted.

In some illustrative embodiments, the invention is related to a method for treating a patient with a bacterial infection comprising the step of administrating therapeutically effective amount of a carbonic anhydrase inhibitor or a pharmaceutically acceptable salt thereof, together with one or more diluents, excipients or carriers, to the patient in need of treatment for said infection, wherein said carbonic anhydrase inhibitor is

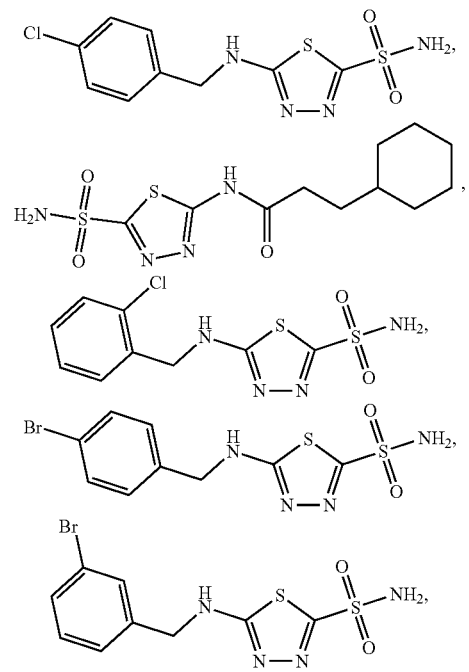

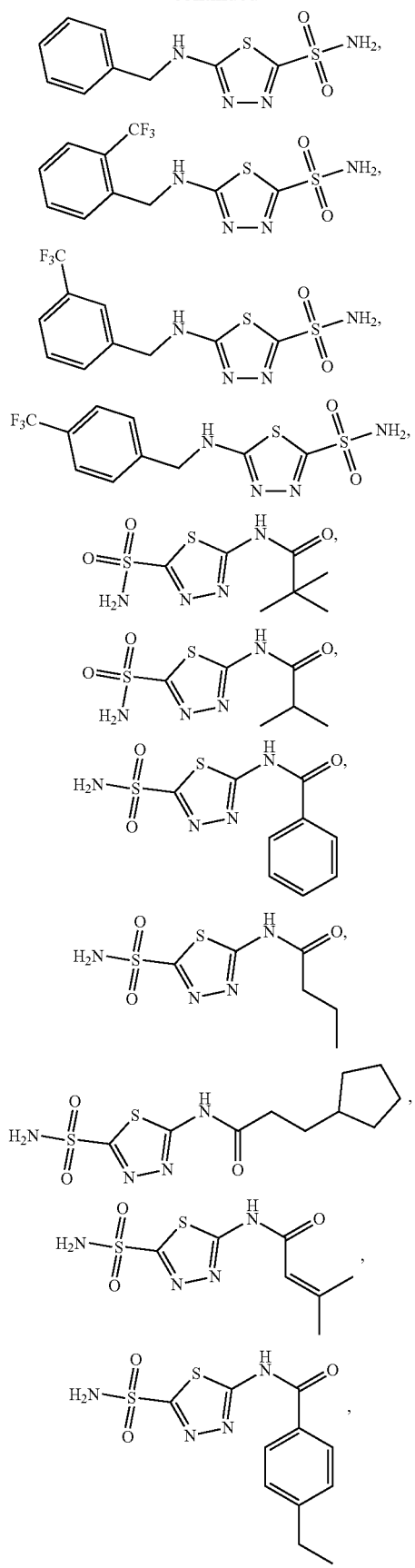
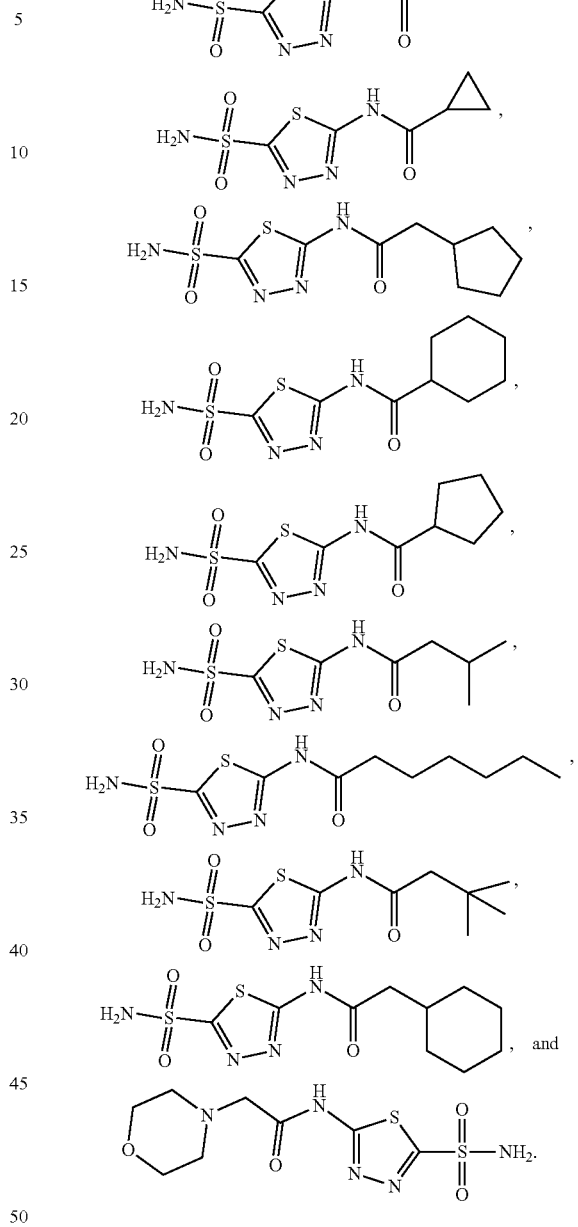

In some illustrative embodiments, the invention is related to a method for decolonizing a patient with a bacterial infection comprising the step of administrating therapeutically effective amount of a carbonic anhydrase inhibitor or a pharmaceutically acceptable salt thereof, together with one or more diluents, excipients or carriers, to the patient in need of treatment.

In some illustrative embodiments, the invention is related to a method for decolonizing a patient with a bacterial infection comprising the step of administrating therapeutically effective amount of a carbonic anhydrase inhibitor or a pharmaceutically acceptable salt thereof, together with one or more diluents, excipients or carriers, to the patient in need of treatment, wherein said carbonic anhydrase inhibitor has the formula (I)

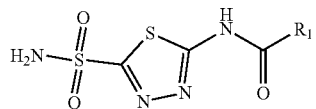
(I)

or a pharmaceutically acceptable salt thereof, wherein
R₁ is an alkyl, alkenyl, alkynyl, heteroalkyl, heteroalkenyl, heterocyclyl, cycloalkyl, cycloalkenyl, cycloheteroalkyl, cycloheteroalkenyl, alkylaryl, alkenylaryl, aryl, arylalkyl, and arylalkenyl, each of which is optionally substituted.

In some illustrative embodiments, the invention is related to a method for decolonizing a patient with a bacterial infection comprising the step of administrating therapeutically effective amount of a carbonic anhydrase inhibitor or a pharmaceutically acceptable salt thereof, together with one or more diluents, excipients or carriers, to the patient in need of treatment, wherein said carbonic anhydrase inhibitor is

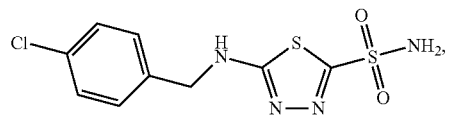
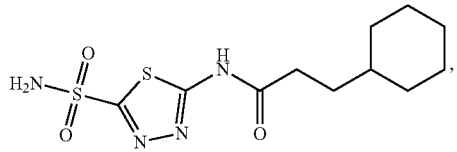
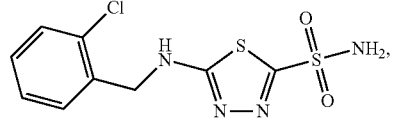
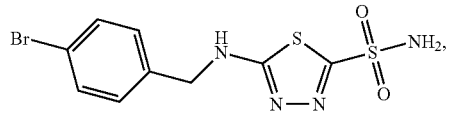
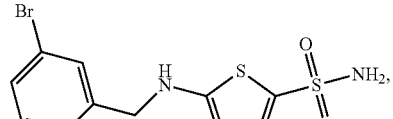
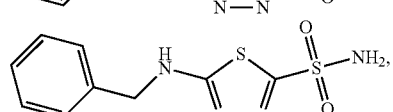
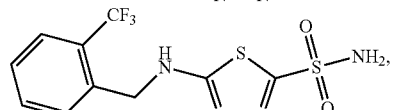
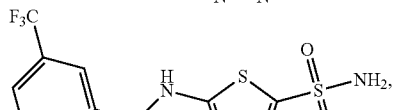
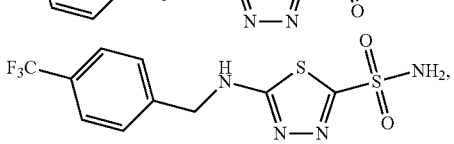

-continued

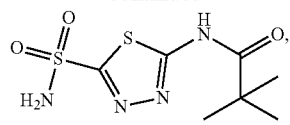
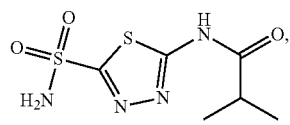
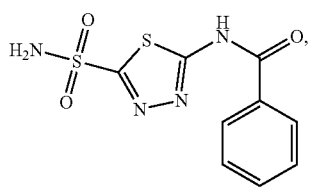
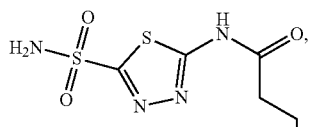
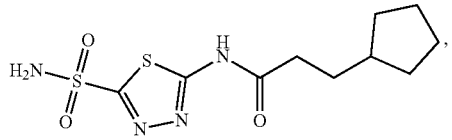
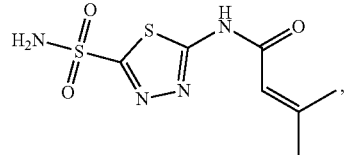
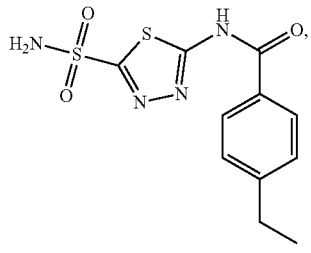
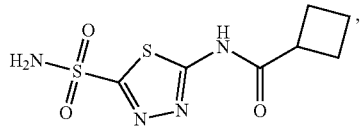
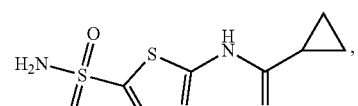
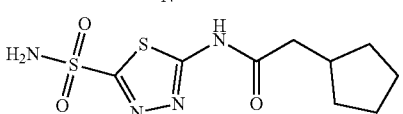
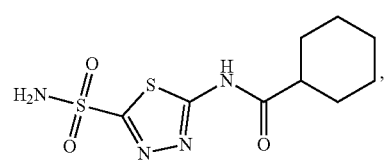

-continued

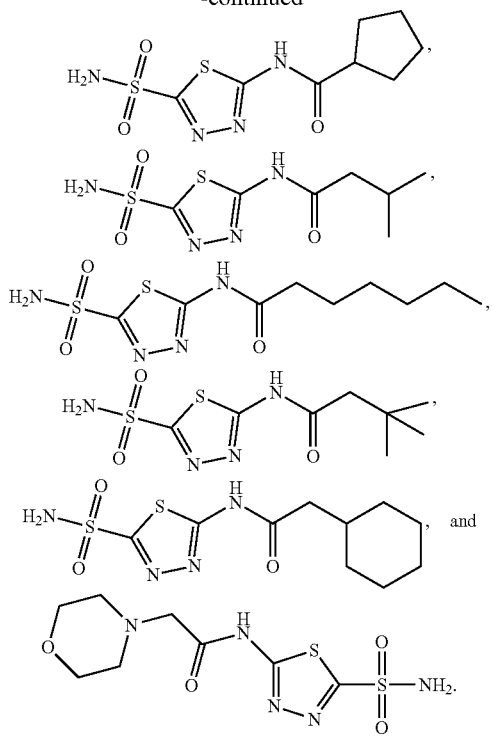

In some illustrative embodiments, the invention is related to a method for treating a patient with a symptom caused a bacterial infection comprising the step of administrating therapeutically effective amount of a carbonic anhydrase inhibitor or a pharmaceutically acceptable salt thereof, together with one or more diluents, excipients or carriers, to the patient in need of treatment, wherein said symptom is an inflammatory bowel disease or autoimmune disease.

In some illustrative embodiments, the invention is related to a method for treating a patient with a symptom caused a bacterial infection comprising the step of administrating therapeutically effective amount of a carbonic anhydrase inhibitor or a pharmaceutically acceptable salt thereof, together with one or more diluents, excipients or carriers, to the patient in need of treatment, wherein said symptom is an inflammatory bowel disease or autoimmune disease, wherein said carbonic anhydrase inhibitor has the formula (I)

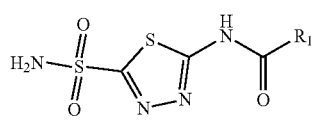

(I)

or a pharmaceutically acceptable salt thereof, wherein
R$_1$ is an alkyl, alkenyl, alkynyl, heteroalkyl, heteroalkenyl, heterocyclyl, cycloalkyl, cycloalkenyl, cycloheteroalkyl, cycloheteroalkenyl, alkylaryl, alkenylaryl, aryl, arylalkyl, and arylalkenyl, each of which is optionally substituted.

In some illustrative embodiments, the invention is related to a method for treating a patient with a symptom caused a bacterial infection comprising the step of administrating therapeutically effective amount of a carbonic anhydrase inhibitor or a pharmaceutically acceptable salt thereof, together with one or more diluents, excipients or carriers, to the patient in need of treatment, wherein said symptom is an inflammatory bowel disease or autoimmune disease, wherein said carbonic anhydrase inhibitor is

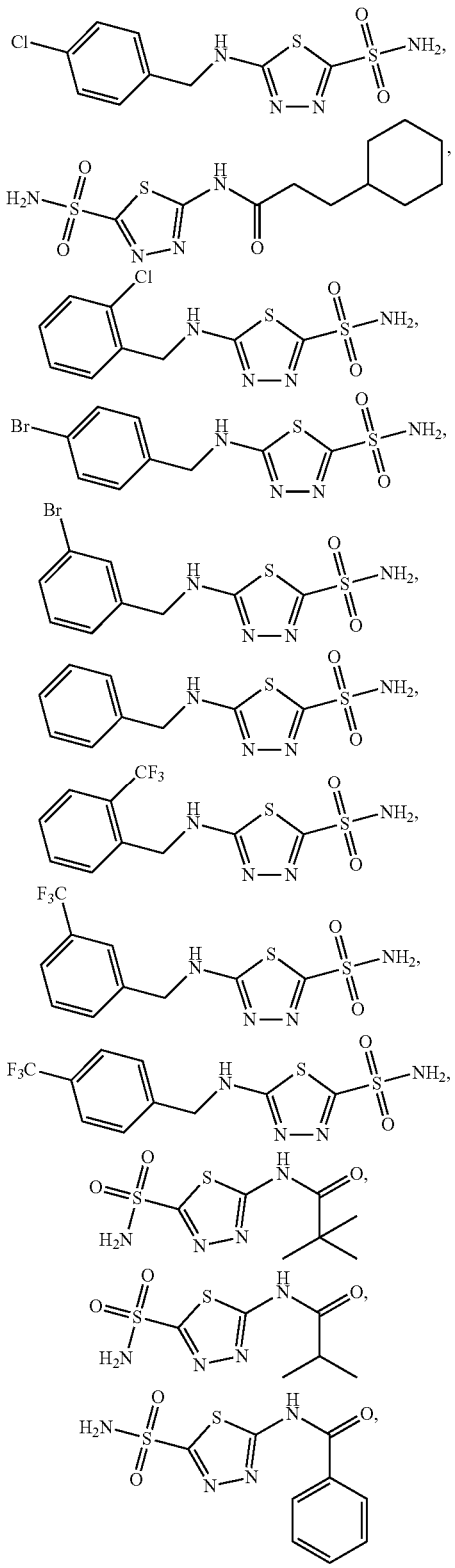

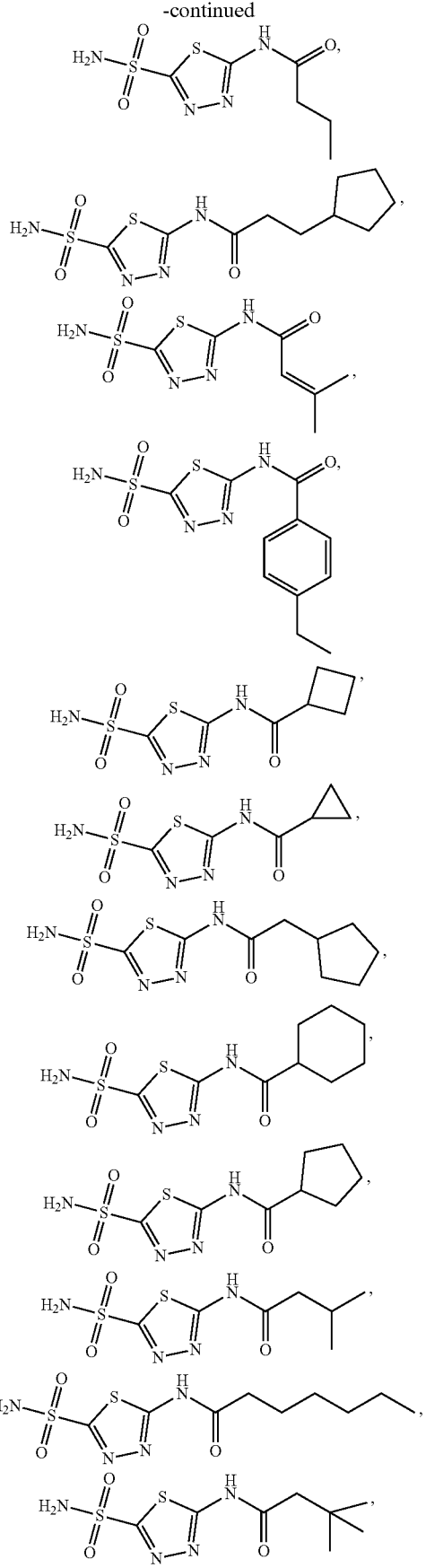
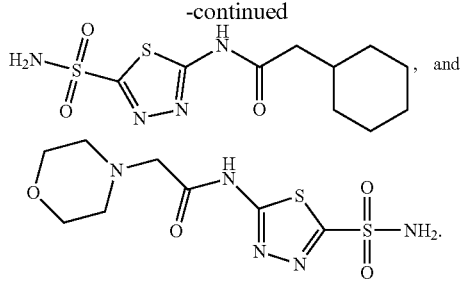

In some illustrative embodiments, the invention is related to a method for treating a patient with a bacterial infection comprising the step of administrating therapeutically effective amount of a carbonic anhydrase inhibitor or a pharmaceutically acceptable salt thereof, together with one or more diluents, excipients or carriers, to the patient in need of treatment for said infection, wherein said bacterial infection is an infection caused by a vancomycin-resistant or vancomycin susceptible bacteria.

In some illustrative embodiments, the invention is related to a method for treating a patient with a bacterial infection comprising the step of administrating therapeutically effective amount of a carbonic anhydrase inhibitor or a pharmaceutically acceptable salt thereof, together with one or more diluents, excipients or carriers, to the patient in need of treatment for said infection, wherein said bacteria is an *Enterococcus* species.

In some illustrative embodiments, the invention is related to a method for treating a patient with a bacterial infection comprising the step of administrating therapeutically effective amount of a carbonic anhydrase inhibitor or a pharmaceutically acceptable salt thereof, together with one or more diluents, excipients or carriers, to the patient in need of treatment for said infection, wherein said *Enterococcus* species comprises *Enterococcus faecium, Enterococcus faecalis*, or *Enterococcus gallinarum, Enterococcus casseliflavus, Enterococcus durans, Enterococcus hirae, Enterococcus saccharolyticus*, and *Enterococcus raffinosus*.

In some illustrative embodiments, the invention is related to a method for decolonizing a patient with a bacterial infection comprising the step of administrating therapeutically effective amount of a carbonic anhydrase inhibitor or a pharmaceutically acceptable salt thereof, together with one or more diluents, excipients or carriers, to the patient in need of treatment, wherein said bacterial infection is an infection caused by a vancomycin-resistant or vancomycin susceptible bacteria.

In some illustrative embodiments, the invention is related to a method for decolonizing a patient with a bacterial infection comprising the step of administrating therapeutically effective amount of a carbonic anhydrase inhibitor or a pharmaceutically acceptable salt thereof, together with one or more diluents, excipients or carriers, to the patient in need of treatment, wherein said bacteria is an *Enterococcus* species.

In some illustrative embodiments, the invention is related to a method for decolonizing a patient with a bacterial infection comprising the step of administrating therapeutically effective amount of a carbonic anhydrase inhibitor or a pharmaceutically acceptable salt thereof, together with one or more diluents, excipients or carriers, to the patient in need of treatment, wherein said *Enterococcus* species comprises *Enterococcus faecium, Enterococcus faecalis*, or *Enterococ-* cus gallinarum, Enterococcus casseliflavus, Enterococcus durans, Enterococcus hirae, Enterococcus saccharolyticus, and Enterococcus raffinosus.

In some illustrative embodiments, the invention is related to a method for treating a patient with a symptom caused a bacterial infection comprising the step of administrating therapeutically effective amount of a carbonic anhydrase inhibitor or a pharmaceutically acceptable salt thereof, together with one or more diluents, excipients or carriers, to the patient in need of treatment, wherein said symptom is an inflammatory bowel disease or autoimmune disease, wherein said bacterial infection is an infection caused by a vancomycin-resistant or vancomycin susceptible bacteria.

In some illustrative embodiments, the invention is related to a method for treating a patient with a symptom caused a bacterial infection comprising the step of administrating therapeutically effective amount of a carbonic anhydrase inhibitor or a pharmaceutically acceptable salt thereof, together with one or more diluents, excipients or carriers, to the patient in need of treatment, wherein said symptom is an inflammatory bowel disease or autoimmune disease, wherein said bacteria is an *Enterococcus* species.

In some illustrative embodiments, the invention is related to a method for treating a patient with a symptom caused a bacterial infection comprising the step of administrating therapeutically effective amount of a carbonic anhydrase inhibitor or a pharmaceutically acceptable salt thereof, together with one or more diluents, excipients or carriers, to the patient in need of treatment, wherein said symptom is an inflammatory bowel disease or autoimmune disease, wherein said *Enterococcus* species comprises *Enterococcus faecium, Enterococcus faecalis,* or *Enterococcus gallinarum, Enterococcus casseliflavus, Enterococcus durans, Enterococcus hirae, Enterococcus saccharolyticus,* and *Enterococcus raffinosus.*

In some illustrative embodiments, the invention is related to a compound having the formula (I)

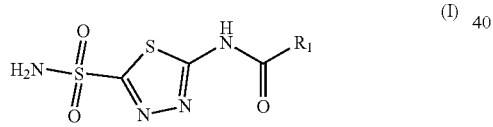

(I)

or a pharmaceutically acceptable salt thereof, wherein
R₁ is an alkyl, alkenyl, alkynyl, heteroalkyl, heteroalkenyl, heterocyclyl, cycloalkyl, cycloalkenyl, cycloheteroalkyl, cycloheteroalkenyl, alkylaryl, alkenylaryl, aryl, arylalkyl, and arylalkenyl, each of which is optionally substituted.

In some illustrative embodiments, the invention is related to a compound having the formula (I), wherein said compound is

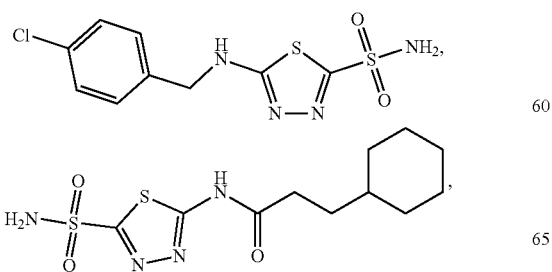

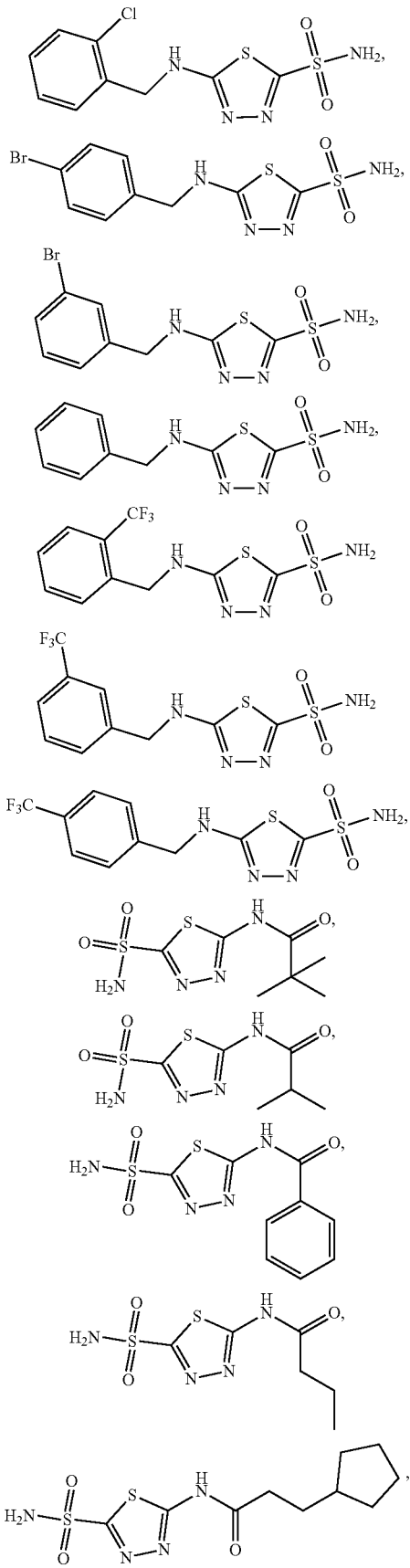

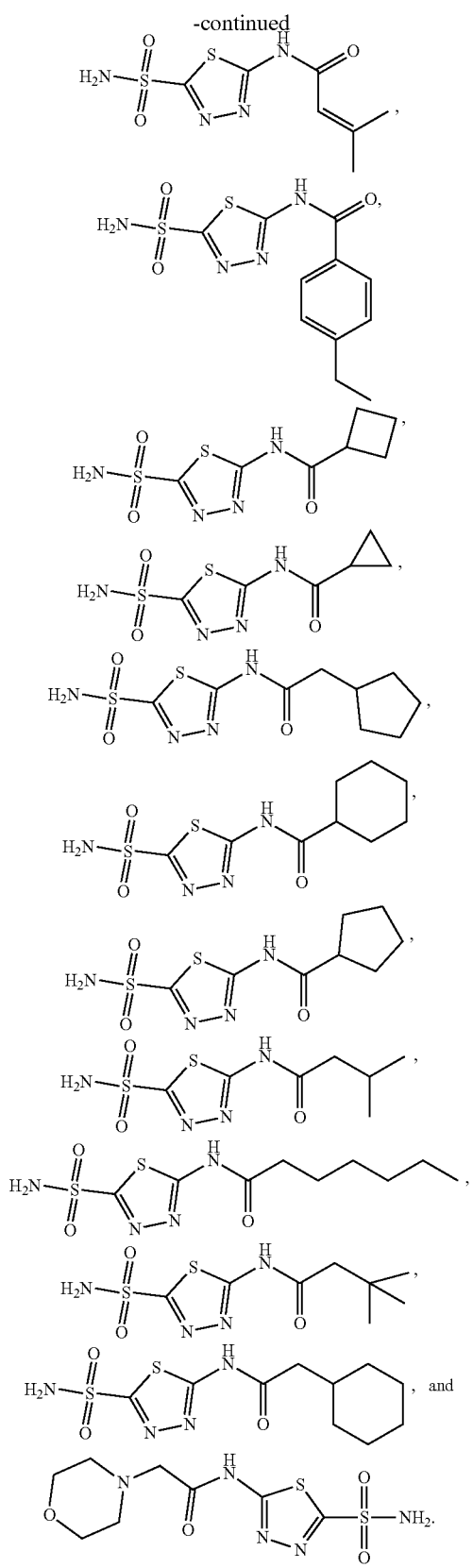

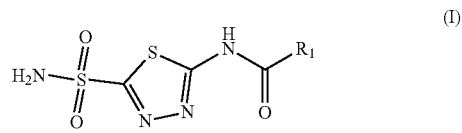

In some other illustrative embodiments, the present invention relates to a pharmaceutical composition comprising one or more compounds of formula (I) as disclosed herein, or a pharmaceutically acceptable salt thereof, together with one or more diluents, excipients or carriers.

In some other illustrative embodiments, the present invention relates to a pharmaceutical composition comprising one or more compounds of formula (I) as disclosed herein, or a pharmaceutically acceptable salt thereof, together with one or more diluents, excipients or carriers, for use as a medicament.

In some other illustrative embodiments, the present invention relates to a pharmaceutical composition comprising one or more compounds of formula (I) as disclosed herein, or a pharmaceutically acceptable salt thereof, together with one or more diluents, excipients or carriers, for use in the treatment of a bacterial infection.

In some other illustrative embodiments, the present invention relates to a method for treating a patient with a bacterial infection comprising the step of administrating therapeutically effective amount of a carbonic anhydrase inhibitor or a pharmaceutically acceptable salt thereof, in combination with one or more other compounds of the same or different mode of action, together with one or more diluents, excipients or carriers, to the patient in need of treatment for said infection.

In some other illustrative embodiments, the present invention relates to a method for decolonizing a patient with a bacterial infection comprising the step of administrating therapeutically effective amount of a carbonic anhydrase inhibitor or a pharmaceutically acceptable salt thereof, in combination with one or more other compounds of the same or different mode of action, together with one or more diluents, excipients or carriers, to the patient in need of treatment.

In some other illustrative embodiments, the present invention relates to a method for treating a patient with a symptom caused a bacterial infection comprising the step of administrating therapeutically effective amount of a carbonic anhydrase inhibitor or a pharmaceutically acceptable salt thereof, in combination with one or more other compounds of the same or different mode of action, together with one or more diluents, excipients or carriers, to the patient in need of treatment, wherein said symptom is an inflammatory bowel disease or autoimmune disease.

In some other illustrative embodiments, the present invention relates to a pharmaceutical composition disclosed herein, wherein said carbonic anhydrase inhibitor has the formula (I)

$$\underset{H_2N-S}{\overset{O}{\underset{\parallel}{\|}}}\overset{S}{\underset{N-N}{\bigvee}}\overset{H}{\underset{O}{\bigvee}}R_1 \qquad (I)$$

or a pharmaceutically acceptable salt thereof, wherein

R$_1$ is an alkyl, alkenyl, alkynyl, heteroalkyl, heteroalkenyl, heterocyclyl, cycloalkyl, cycloalkenyl, cycloheteroalkyl, cycloheteroalkenyl, alkylaryl, alkenylaryl, aryl, arylalkyl, and arylalkenyl, each of which is optionally substituted.

In some other illustrative embodiments, the present invention relates to a pharmaceutical composition disclosed herein, wherein said carbonic anhydrase inhibitor is

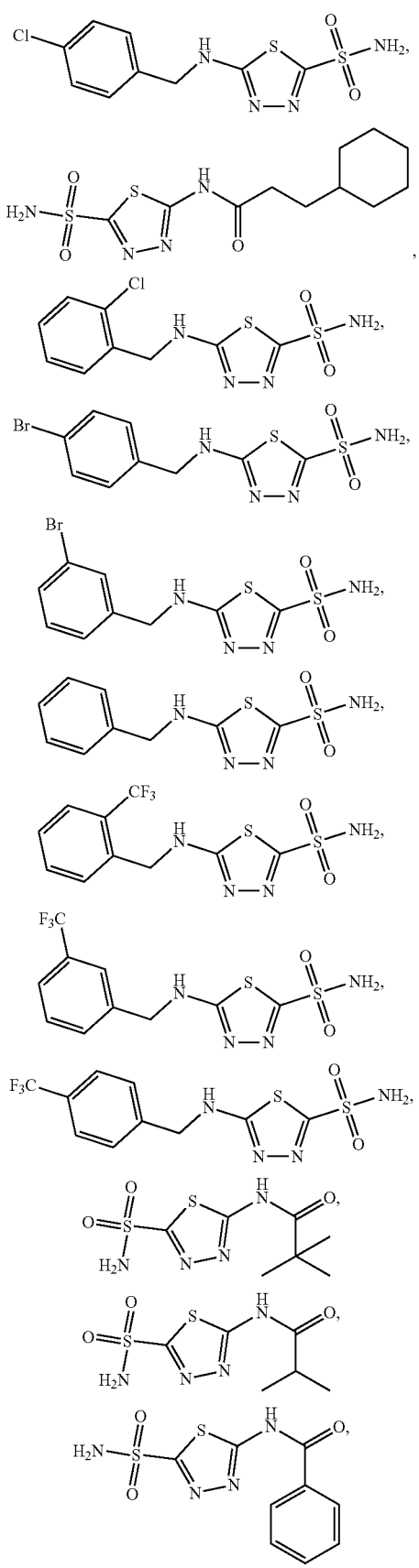
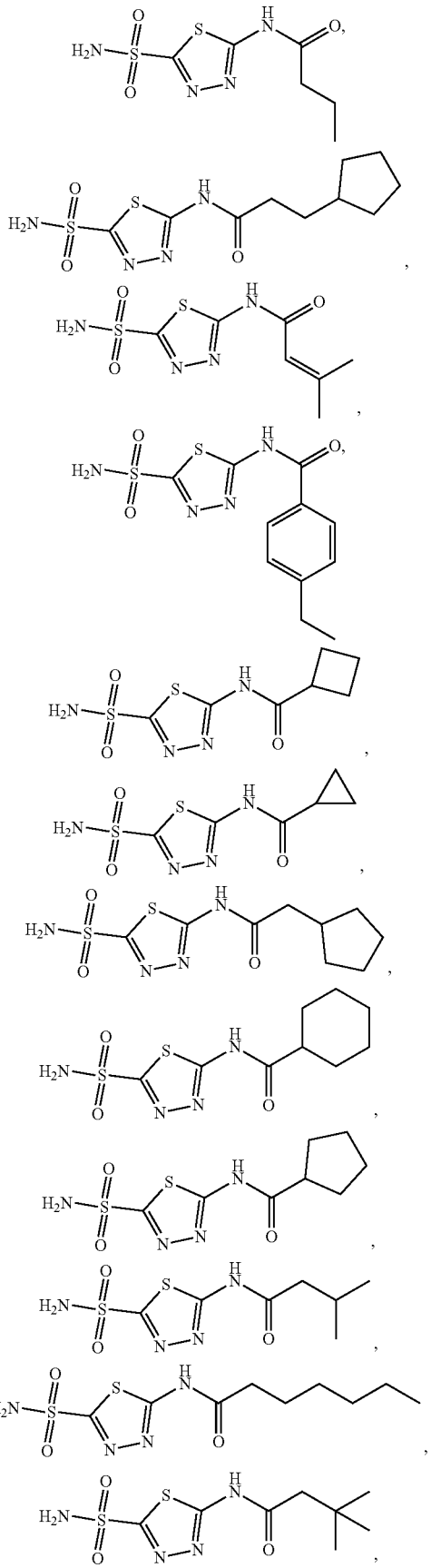

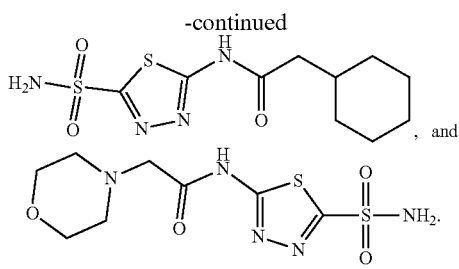
, and

In another embodiment, pharmaceutical compositions containing one or more of the compounds are also described herein. In one aspect, the compositions include a therapeutically effective amount of the one or more compounds for treating a patient with infection. It is to be understood that the compositions may include other component and/or ingredients, including, but not limited to, other therapeutically active compounds with the same or different modes of action, and one or more carriers, diluents, excipients, and the like. In another embodiment, methods for using the compounds and pharmaceutical compositions for treating patients with infection are also described herein. In one aspect, the methods include the step of administering one or more of the compounds and/or compositions described herein to a patient with infection. In another aspect, the methods include administering a therapeutically effective amount of the one or more compounds and/or compositions described herein for treating patients with infection.

The following non-limiting exemplary embodiments are included herein to further illustrate the invention. These exemplary embodiments are not intended and should not be interpreted to limit the scope of the invention in any way. It is also to be understood that numerous variations of these exemplary embodiments are contemplated herein.

Chemistry. 1H and $^{13}$C NMR spectra were recorded on Bruker DRX500 spectrometer (operating at 500 and 126 MHz) in DMSO-$d_6$ with or without the internal standard of TMS at 0.05% v/v. The chemical shifts (δ) reported as parts per million (ppm) and the coupling constants are reported as s=singlet, bs=broad singlet, d=doublet, t=triplet, q=quartet, dd=doublet of doublet, m=multiplet. The purity of all final compounds was >95% purity as assessed by HPLC according to current American Chemical Society guidelines for publication. Final compounds were analyzed on an Agilent 1200 series chromatograph. The chromatographic method utilized as ThermoScientific Hypersil GOLD C-18 or silica column. UV detection wavelength=220/254 nm; flow-rate=1.0 mL/min; solvent=acetonitrile/water for reverse phase and ethyl acetate/hexane for normal phase. Both organic and aqueous mobile phases contain 0.1% v/v formic acid. The mass spectrometer used is an AB Sciex 4500 QTrap triple-quadrupole mass spectrometer with an ESI source or an Advion CMS-L Compact Mass Spectrometer with an ESI or an APCI source. Samples are submitted for analysis solubilized in 1:1 acetonitrile:water solution or using the atmospheric solids analysis probe (ASAP). Compounds were generally prepared according to scheme 1 and protocols are detailed below.

Scheme 1:

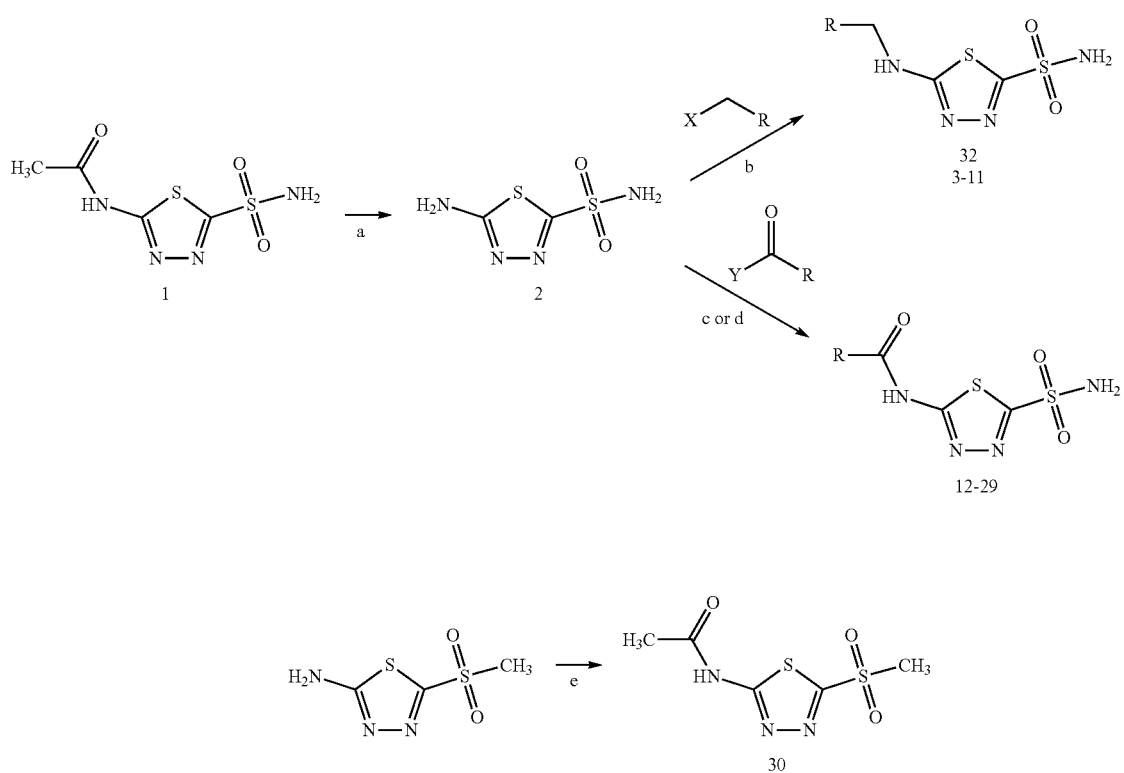

X = Br or I
Y = Cl or OH
R = alkyl, cycloalkyl, substituted or unsubstituted aromatic Reagents: (a) HCl, 100° C., 14 h; (b) potassium carbonate, acetonitrile, 60° C., 2-16 h; (c) if X=OH: oxalyl chloride, dry DMF, dry DCM, 0° C.-rt, 1-2 h, crude product carried into next step; (d) if X=Cl: triethylamine, dry acetonitrile, room temperature, 14-16 h; (e) acetic anhydride, acetic acid, 60° C., 1 h.

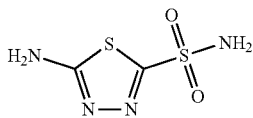

2

5-amino-1,3,4-thiadiazole-2-sulfonamide (2). To a 100 mL roundbottom flask was added 1 (2.07 g, 9.3 mmol, 1 eq.) and concentrated HCl (10 mL, 120 mmol, 13 eq) to form a white suspension. The reaction was refluxed at 95° C. and the white suspension became a colorless solution. After 24 h the reaction was cooled to rt and a white precipitate began to form. The reaction was removed from stirring and the white precipitate was allowed to settle. The excess HCl was decanted off and the remaining solid suspension containing as little HCl as possible was cooled in ice bath. This suspension was neutralized to pH 7 with 5.0 M aqueous NaOH solution. The white precipitate was filtered out by vacuum filtration to afford 2 as a white solid (1.23 g, 6.8 mmol, 74%). $^1$H NMR (500 MHZ, DMSO-$d_6$): δ 8.08 (s, 2H), 7.83 (s, 2H).

The following procedure was carried out for analogs 3-11 and is detailed for compound (3, AT3-006-2-3). All other analogs followed this protocol unless otherwise noted.

Procedure 1: 5-((4-chlorobenzyl)amino)-1,3,4-thiadiazole-2-sulfonamide (3, AT3-006-2-3). To a vial was added 2 (0.096 g, 0.54 mmol, 1.1 eq.), 1-(bromomethyl)-4-chlorobenzene (0.10 g, 0.50 mmol, 1 eq.), potassium carbonate (0.082 g, 0.60 mmol, 1.2 eq.) and acetonitrile (3 mL). The reaction as stirred at 60° C. for 18 h then cooled to rt, concentrated in vacuo and purified by normal phase flash chromatography (0-20% ethyl acetate: DCM) to provide 3 (0.044 g, 0.139 mmol, 28%) a white solid. $^1$H NMR (500 MHZ, DMSO-$d_6$): δ 8.08 (s, 1H), 7.28 (d, 2H), 7.17 (d, 2H), 4.46 (s, 2H). $^{13}$C NMR (126 MHZ, DMSO-$d_6$): d 172.2, 153.5, 134.8, 132.2, 130.2, 128.2, 51.8. APCI-MS: m/z 305.0 [M+H]$^+$ and 307.0 [M+2+H]$^+$. HPLC retention time: 13.474 min. HPLC Purity: 95.5%.

The following procedure was carried out for analogs 12-29 and is detailed for compound (20, JK5-VRE-004). All other analogs followed this protocol unless otherwise noted.

Procedure 2: Step 1 (for use with carboxylic acid containing starting materials). 3-cyclohexyl-N-(5-sulfamoyl-1,3,4-thiadiazol-2-yl) propenamide (20, JK5-VRE-004). To a vial was added the 3-cyclohexylpropanoic acid (0.038 mg, 1.1 eq., 0.24 mmol) in DCM (0.5 ml) followed by 1 drop of DMF. The reaction mixture was then cooled to 0° C. followed by slow addition of oxalyl chloride (0.034 mg, 1.2 eq., 0.27 mmol). The reaction was then allowed to warm at room temperature and was stirred for 2 hours. After the completion of reaction, it was concentrated in vacuo and carried into the amide coupling reaction without purification. If the acyl chloride is commercially available, then the oxalyl chloride step can be bypassed.

Step 2: To an argon flushed vial was added 5-amino-1,3,4-thiadiazole-2-sulfonamide (0.040 mg, 1 eq., 0.22 mmol) dissolved in 1 ml of acetonitrile, followed by triethylamine (0.027 mg, 1.2 eq., 0.27 mmol) at 0° C. The concentrated acyl chloride was then diluted with acetonitrile (0.2 mL) and added drop-wise to the reaction mixture at 0° C. The reaction mixture was stirred for 14 hours at room temperature. The reaction mixture was then worked up using DCM and washed with 2N HCl, followed by brine and was further purified by normal phase chromatography (0-100% ethyl acetate: hexane) to afford desired product 20 as a white solid (0.030 g, 0.094 mmol, 42%). $^1$H NMR (500 MHZ, DMSO-$d_6$): δ 13.00 (s, 1H), 8.33 (s, 2H, NH$_2$), 2.54 (t, J=7.5 Hz, 2H, CH$_2$), 1.74-1.63 (m, 4H, 2×CH$_2$), 1.52-163 (m, 3H, CH$_2$+CH), 1.24-1.06 (m, 4H, 2×CH$_2$), 0.89-0.84 (m, 2H, CH$_2$). $^{13}$C NMR (126 MHz, DMSO-$d_6$): δ 172.84, 164.56, 161.39, 36.90, 32.77, 32.13, 26.37, 26.01. APCI-MS: m/z 319.1 [M+H]$^+$. HPLC retention time: 12.322 min. HPLC Purity: 100%.

5-((2-chlorobenzyl)amino)-1,3,4-thiadiazole-2-sulfonamide (4, AT3-009). Prepared according to procedure 1 using 2 (0.096 g, 0.54 mmol, 1.1 eq.), 1-(bromomethyl)-2-chlorobenzene (0.10 g, 0.50 mmol, 1 eq.), potassium carbonate (0.082 g, 0.60 mmol, 1.2 eq.) to produce 4 (0.038 g, 0.13 mmol, 27%). $^1$H NMR (500 MHZ, DMSO-$d_6$): δ 8.11 (s, 1H), 7.40-7.34 (m, 1H), 7.30-7.22 (m, 1H), 7.20-7.13 (m, 2H), 4.62 (s, 2H). $^{13}$C NMR (126 MHz, DMSO-$d_6$): δ 172.3, 152.9, 132.9, 132.4, 130.1, 129.3, 129.1, 126.9, 50.4. APCI-MS: m/z 305.0 [M+H]$^+$ and 307.0 [M+2+H]$^+$. HPLC retention time: 12.911 min. HPLC Purity: 98.9%.

5-((4-bromobenzyl)amino)-1,3,4-thiadiazole-2-sulfonamide (5, AT3-010). Prepared according to procedure 1 using 2 (0.063 g, 0.34 mmol, 1.0 eq.), 1-bromo-4-(bromomethyl) benzene (0.094 g, 0.38 mmol, 1.1 eq.), potassium carbonate (0.052 g, 0.38 mmol, 1.1 eq.) to produce 5 (0.063 g, 0.18 mmol, 52%). $^1$H NMR (500 MHZ, DMSO-$d_6$): δ 8.07 (s, 1H), 7.47-7.36 (m, 2H), 7.16-7.06 (m, 2H), 4.44 (s, 2H). $^{13}$C NMR (126 MHZ, DMSO-$d_6$): δ 172.2, 153.5, 135.2, 131.1, 130.5, 120.8, 51.8. APCI-MS: m/z 349.0 [M+H]$^+$ and 351.0 [M+2+H]$^+$. HPLC retention time: 12.105 min. HPLC Purity: 98.6%.

5-((3-bromobenzyl)amino)-1,3,4-thiadiazole-2-sulfonamide (6, AT3-011). Prepared according to procedure 1 using 2 (0.050 g, 0.28 mmol, 1.0 eq.), 1-bromo-3-(bromomethyl) benzene (0.076 g, 0.31 mmol, 1.1 eq.), potassium carbonate (0.042 g, 0.31 mmol, 1.1 eq.) to produce 6 (0.059 g, 0.17 mmol, 60%). $^1$H NMR (500 MHZ, DMSO-$d_6$): δ 8.09 (s, 1H), 7.37-7.36 (m, 1H), 7.29 (m, 1H), 7.22-7.12 (m, 2H), 4.49 (s, 2H). $^{13}$C NMR (126 MHz, DMSO-$d_6$): δ 172.2, 153.4, 138.6, 131.0, 130.4, 130.2, 127.3, 121.5, 52.2. APCI-MS: m/z 349.0 [M+H]$^+$ and 351.0 [M+2+H]$^+$. HPLC retention time: 13.491 min. HPLC Purity: 99.0%.

5-(benzylamino)-1,3,4-thiadiazole-2-sulfonamide (7, AT3-013). Prepared according to procedure 1 using 2 (0.052 g, 0.29 mmol, 1.0 eq.), (bromomethyl)benzene (0.054 g, 0.32 mmol, 1.1 eq.), potassium carbonate (0.043 g, 0.32 mmol, 1.1 eq.) to produce 7 (0.027 g, 0.10 mmol, 35%). $^1$H NMR (500 MHZ, DMSO-$d_6$): δ 8.03 (s, 1H), 7.28-7.21 (m, 3H), 7.16 (dd, J=7.4, 2.1 Hz, 2H), 4.44 (s, 2H). $^{13}$C NMR (126 MHz, DMSO-$d_6$): δ 172.1, 154.0, 135.6, 128.3, 128.3, 127.6, 51.9. APCI-MS: m/z 271.0 [M+H]$^+$. HPLC retention time: 12.295 min. HPLC Purity: 99.3%.

5-((2-(trifluoromethyl)benzyl) amino)-1,3,4-thiadiazole-2-sulfonamide (8, AT3-014). Prepared according to procedure 1 using 2 (0.057 g, 0.32 mmol, 1.0 eq.), 1-(bromomethyl)-2-(trifluoromethyl)benzene (0.090 g, 0.38 mmol, 1.2 eq.), potassium carbonate (0.052 g, 0.38 mmol, 1.2 eq.) to produce 8 (0.018 g, 0.053 mmol, 17%). $^1$H NMR (500 MHZ, DMSO-$d_6$): δ 8.11 (s, 1H), 7.56 (dd, J=7.9, 1.3 Hz, 1H), 7.54-7.50 (m, 1H), 7.48 (dd, J=7.4, 1.3 Hz, 1H), 7.38-7.33 (m, 1H), 4.71 (s, 2H). $^{13}$C NMR (126 MHZ, DMSO-$d_6$): δ

172.4, 152.7, 133.8, 132.4, 129.8, 128.1, 126.3 (q, J=31.9 Hz), 125.8 (q, J=6.3 Hz), 124.0 (q, J=277.2 Hz), 49.3. APCI-MS: m/z 339.1 [M+H]⁺. HPLC retention time: 12.295 min. HPLC Purity: 99.3%.

5-((3-(trifluoromethyl)benzyl) amino)-1,3,4-thiadiazole-2-sulfonamide (9, AT3-015). Prepared according to procedure 1 using 2 (0.046 g, 0.26 mmol, 1.0 eq.), 1-(bromomethyl)-3-(trifluoromethyl)benzene (0.12 g, 0.52 mmol, 1.2 eq.), potassium carbonate (0.042 g, 0.31 mmol, 1.2 eq.) to produce 9 (0.033 g, 0.098 mmol, 38%). ¹H NMR (500 MHZ, DMSO-d₆): δ 8.12 (s, 1H), 7.47 (dd, J=7.6, 1.7 Hz, 2H), 7.40 (d, J=7.6 Hz, 1H), 7.36 (d, J=1.8 Hz, 1H), 4.63 (s, 2H). ¹³C NMR (126 MHz, DMSO-d₆): δ 172.3, 153.1, 137.5, 132.4, 129.2, 128.9 (q, J=31.5 Hz), 124.72, 124.15, 123.8 (q, J=272.7 Hz), 52.88. APCI-MS: m/z 339.1 [M+H]⁺. HPLC retention time: 13.389 min. HPLC Purity: 96.4%.

5-((4-(trifluoromethyl)benzyl) amino)-1,3,4-thiadiazole-2-sulfonamide (10, AT3-016). Prepared according to procedure 1 using 2 (0.052 g, 0.29 mmol, 1.0 eq.), 1-(bromomethyl)-4-(trifluoromethyl)benzene (0.082 g, 0.35 mmol, 1.2 eq.), potassium carbonate (0.047 g, 0.35 mmol, 1.2 eq.) to produce 10 (0.041 g, 0.12 mmol, 41%). ¹H NMR (500 MHZ, DMSO-d₆): δ 8.10 (s, 1H), 7.47 (d, J=8.2 Hz, 2H), 7.33 (d, J=8.1 Hz, 2H), 4.60 (s, 2H). ¹³C NMR (126 MHz, DMSO-d₆): δ 172.3, 153.2, 140.6, 129.1, 128.0 (q, J=31.5 Hz), 124.8 (q, J=3.9 Hz), 124.0 (q, J=272.2 Hz), 52.7. APCI-MS: m/z 339.1 [M+H]⁺. HPLC retention time: 13.548 min. HPLC Purity: 99.0%.

N-(5-Sulfamoyl-1,3,4-thiadiazol-2-yl) propionamide (11, AS-004A). Isolated as a white solid (0.022 g, 0.092 mmol, 33%). ¹H NMR (500 MHZ, DMSO-d₆): δ 12.98 (s, 1H, NH), 8.34 (s, 2H, NH₂), 2.56-2.52 (m, 2H, CH₂), 1.11 (t, J=7.5 Hz, 3H, CH₃). ¹³C NMR (126 MHz, DMSO-d₆) δ 173.3, 164.5, 161.5, 28.5, 9.1. ESI-MS: m/z 236.6 [M+H]⁺. HPLC retention time: 11.457 min. HPLC Purity: 95.6%.

N-(5-Sulfamoyl-1,3,4-thiadiazol-2-yl) pivalamide (12, AS-004B). Isolated as a white solid (0.021 g, 0.080 mmol, 29%). ¹H NMR (500 MHz, DMSO-d₆): δ 12.75 (s, 1H, NH), 8.33 (s, 2H, NH₂), 1.27 (s, 9H, 3×CH₃). ¹³C NMR (126 MHz, DMSO-d₆) δ 173.5, 162.7, 159.2, 38.8, 28.5. APCI-MS: m/z 264.9 [M+H]⁺. HPLC retention time: 10.230 min. HPLC Purity: 99.2%

N-(5-Sulfamoyl-1,3,4-thiadiazol-2-yl) isobutyramide (13, AS-005A). Isolated as a white solid (0.049 g, 0.20 mmol, 71%). ¹H NMR (500 MHZ, DMSO-d₆): δ 13.01 (s, 1H, NH), 8.34 (s, 2H, NH₂), 2.84-2.79 (m, 1H, CH), 1.15 (d, J=6.8 Hz, 6H, 2×CH₃). ¹³C NMR (126 MHZ, DMSO-d₆) δ 176.4, 164.7, 161.6, 34.3, 19.2. ESI-MS: m/z 250.6 [M+H]⁺. HPLC retention time: 9.553 min. HPLC Purity: 100%.

N-(5-Sulfamoyl-1,3,4-thiadiazol-2-yl)benzamide (14, AS-005B). Isolated as a white solid (0.0035 g, 0.012 mmol, 4.5%). ¹H NMR (500 MHZ, DMSO-d₆): δ 13.56 (s, 1H, NH), 8.37 (s, 2H, NH₂), 8.19-8.12 (m, 2H, 2×CH), 7.73-7.66 (m, 1H, CH), 7.61-7.58 (m, 2H, 2×CH). ¹³C NMR (126 MHZ, DMSO-d₆) δ 166.1, 165.0, 162.6, 133.7, 131.3, 129.1, 129.0. APCI-MS: m/z 284.9 [M+H]⁺. HPLC retention time: 10.380 min. HPLC Purity: 100%.

N-(5-Sulfamoyl-1,3,4-thiadiazol-2-yl) butyramide (15, AS-005D). Isolated as a white solid (0.009 g, 0.036 mmol, 17%) ¹H NMR (500 MHZ, DMSO-d₆): δ 12.98 (s, 1H, NH), 8.29 (s, 2H, NH₂), 2.48 (bs, 2H, CH₂), 1.64-1.58 (m, 2H, CH₂), 0.87 (t, J=7.3 Hz, 3H, CH₃). ¹³C: APCI-MS: m/z 251.0 [M+H]⁺ HPLC retention time: 11.457 min. HPLC Purity: 95.6%.

3-Cyclopentyl-N-(5-sulfamoyl-1,3,4-thiadiazol-2-yl) propenamide (16, AS-005H). Isolated as a white solid (0.022 g, 0.076 mmol, 26%). ¹H NMR (500 MHZ, DMSO-d₆): δ 12.98 (s, 1H, NH), 8.29 (s, 2H, NH₂), 2.49 (t, J=7.5 Hz, 2H, CH₂), 1.72-1.67 (m, 3H, CH₂+CH), 1.63-1.54 (bm, 4H, 2×CH₂), 1.47-1.43 (m, 2H, CH₂), 1.05 (bs, 2H, CH₂). ¹³C NMR (126 MHz, DMSO-d₆): δ 172.7, 164.6, 161.4, 39.4, 34.5, 32.3, 30.9, 25.0. APCI-MS: m/z 305.0 [M+H]⁺. HPLC retention time: 11.783 min. HPLC Purity: 99.2%.

3-Methyl-N-(5-sulfamoyl-1,3,4-thiadiazol-2-yl) but-2-enamide (17, AS-005J). Isolated as a white solid (0.025 g, 0.094 mmol, 34%). ¹H NMR (500 MHZ, DMSO-d₆): δ 12.88 (s, 1H, NH), 8.28 (s, 2H, NH₂), 6.00 (s, 1H, CH), 2.19 (s, 3H, CH₃), 1.91 (s, 3H, CH₃). ¹³C NMR (126 MHZ, DMSO-d₆): δ 164.8, 162.2, 160.0, 151.7, 116.7, 28.4, 21.2. APCI-MS: m/z 263.0 [M+H]⁺. HPLC retention time: 10.126 min. HPLC Purity: 95.4%

4-Ethyl-N-(5-sulfamoyl-1,3,4-thiadiazol-2-yl)benzamide (18, AS-005K). Isolated as a white solid (0.030 g, 0.095 mmol, 34%). ¹H NMR (500 MHZ, DMSO-d₆): δ 13.47 (s, 1H, NH), 8.37 (s, 2H, NH₂), 8.09 (d, J=8.3 Hz, 2H, 2×CH), 7.43 (d, J=8.4 Hz, 2H, 2×CH), 2.71 (q, J=7.5 Hz, 2H, CH₂), 1.22 (t, J=7.6 Hz, 3H, CH₃). ¹³C NMR (126 MHZ, DMSO-d₆): δ 165.8, 164.9, 162.6, 150.3, 129.7, 129.1, 128.5, 28.5, 15.5. APCI-MS: m/z 313.0 [M+H]⁺. HPLC retention time: 11.545 min. HPLC Purity: 98.4%

N-(5-Sulfamoyl-1,3,4-thiadiazol-2-yl)cyclobutanecarboxamide (19, JK5-VRE-001-1). Isolated as a white solid (0.026 g, 0.057 mmol, 26%). ¹H NMR (500 MHZ, DMSO-d₆): δ 12.88 (s, 1H, NH), 8.29 (s, 2H, NH₂), 3.43-3.36 (m, 1H, CH), 2.25-2.18 (m, 2H, CH₂), 2.17-2.14 (m, 2H, CH₂), 1.98-1.89 (m, 1H of CH₂), 1.83-1.76 (m, 1H of CH₂). ¹³C NMR (126 MHz, DMSO-d₆): δ 174.03, 164.61, 161.60, 38.51, 24.77, 18.03. ESI-MS: m/z 262.9 [M+H]⁺ HPLC retention time: 11.133 min. HPLC Purity: 100%.

N-(5-Sulfamoyl-1,3,4-thiadiazol-2-yl)cyclopropanecarboxamide (21, JK5-VRE-005). Isolated as a white solid (0.010 g, 0.040 mmol, 21%). ¹H NMR (500 MHz, DMSO-d₆): δ 13.31 (s, 1H, NH), 8.33 (s, 2H, NH₂), 2.06-1.97 (m, 1H, CH), 1.07-1.00 (m, 2H, CH₂), 1.01-0.94 (m, 2H, CH₂). ¹³C NMR (126 MHZ, DMSO-d₆) δ 173.2, 164.6, 161.5, 14.1, 9.6. APCI-MS: m/z 249.0 [M+H]⁺. HPLC retention time: 9.253 min. HPLC Purity: 100%.

2-Cyclopentyl-N-(5-sulfamoyl-1,3,4-thiadiazol-2-yl)acetamide (22, JK5-VRE-006). Isolated as a white solid (0.035 g, 0.12 mmol, 43%). ¹H NMR (500 MHz, DMSO-d₆): δ 12.98 (s, 1H, NH), 8.30 (s, 2H, NH₂), 2.51 (d, J=7.3 Hz, 2H, CH₂), 2.25-2.18 (m, 1H, CH), 1.75-1.69 (m, 2H, CH₂), 1.61-1.54 (m, 2H, CH₂), 1.52-1.45 (m, 2H, CH₂), 1.17-1.10 (m, 2H, CH₂). ¹³C NMR (126 MHZ, DMSO-d₆) & 172.2, 164.6, 161.3, 41.0, 36.5, 32.1, 24.8. APCI-MS: m/z 291.2 [M+H]⁺. HPLC retention time: 11.152 min. HPLC Purity: 100%.

N-(5-Sulfamoyl-1,3,4-thiadiazol-2-yl)cyclohexanecarboxamide (23, AB2-VRE-001). Isolated as a white solid (0.027 g, 0.094 mmol, 34%). ¹H NMR (500 MHZ, DMSO-d₆): δ 12.97 (s, 1H, NH), 8.33 (s, 2H, NH₂), 2.62-2.54 (m, 1H, CH), 1.86 (broad m, 2H, CH₂), 1.74 (broad m, 2H, CH₂), 1.46-1.37 (m, 2H, CH₂), 1.33-1.12 (m, 4H, 2×CH₂). ¹³C NMR (126 MHz DMSO-d₆): δ 175.3, 164.7, 161.5, 43.7, 28.9, 25.5, 25.3. APCI-MS: m/z 291.2 [M+H]⁺. HPLC retention time: 11.043 min. HPLC Purity: 95.2%.

N-(5-Sulfamoyl-1,3,4-thiadiazol-2-yl)cyclopentanecarboxamide (24, AB2-VRE-002). Isolated as a white solid (0.025 g, 0.089 mmol, 32%). ¹H NMR (500 MHZ, DMSO-d₆): § 12.98 (s, 1H, NH), 8.29 (s, 2H, NH₂), 2.99-2.93 (m, 1H, CH), 1.91-1.84 (m, 2H, CH₂), 1.73-1.67 (m, 2H, CH₂), 1.64-1.60 (m, 2H, CH₂), 1.57-1.50 (m, 2H, CH₂). ¹³C NMR (126 MHz, DMSO-d₆) δ 175.6, 164.6, 161.6, 44.2, 30.1, 26.0. APCI-MS: m/z 277.1 [M+H]⁺. HPLC retention time: 10.498 min. HPLC Purity: 99.5%.

3-Methyl-N-(5-sulfamoyl-1,3,4-thiadiazol-2-yl)butanamide (26, AS-005M). Isolated as a white solid (0.036 g, 0.14 mmol, 49%). $^1$H NMR (500 MHZ, DMSO-d$_6$): δ 13.03 (s, 1H, NH), 8.33 (s, 2H, NH$_2$), 2.42 (d, J=7.1 Hz, 2H, CH$_2$), 2.11 (m, 1H, CH), 0.93 (d, J=6.7 Hz, 6H, 2×CH$_3$). $^{13}$C NMR (126 MHZ, DMSO-d$_6$): δ 171.9, 164.6, 161.3, 44.0, 25.7, 22.5. APCI-MS: m/z 265.0 [M+H]⁺. HPLC retention time: 10.306 min. HPLC Purity: 100%.

N-(5-Sulfamoyl-1,3,4-thiadiazol-2-yl)heptanamide (27, AS-005N): Isolated as a white solid (0.027 g, 0.093 mmol, 33.4%). $^1$H NMR (500 MHZ, DMSO-d$_6$): δ 12.96 (s, 1H, NH), 8.29 (s, 2H, NH$_2$), 2.49 (d, J=7.5 Hz, 2H, CH$_2$), 1.60-1.54 (m, 2H, CH$_2$), 1.27-1.19 (m, 6H, 3×CH$_2$), 0.82 (t, J=6.6 Hz, 3H, CH$_3$). $^{13}$C NMR (126 MHZ, DMSO-d$_6$) δ 172.6, 164.6, 161.4, 35.1, 31.2, 28.4, 24.7, 22.2, 14.2. APCI-MS: m/z 293.0 [M+H]⁺. HPLC retention time: 11.758 min. HPLC Purity: 97.7%.

3,3-Dimethyl-N-(5-sulfamoyl-1,3,4-thiadiazol-2-yl)butanamide (28, AS-005L). Isolated as a white solid (0.033 g, 0.12 mmol, 43%). $^1$H NMR (500 MHZ, DMSO-d$_6$): δ 12.98 (s, 1H, NH), 8.32 (s, 2H, NH$_2$), 2.42 (s, 2H, CH$_2$), 1.01 (s, 9H, 3×CH$_3$). $^{13}$C NMR (126 MHz, DMSO-d$_6$): δ 171.2, 164.5, 161.2, 48.1, 31.4, 29.7. APCI-MS: m/z 279.0 [M+H]⁺. HPLC retention time: 10.844 min. HPLC Purity: 100%.

2-Cyclohexyl-N-(5-sulfamoyl-1,3,4-thiadiazol-2-yl)acetamide (29, AS-005W). Isolated as a white solid (0.033 g, 0.11 mmol, 39%). $^1$H NMR (500 MHZ, DMSO-d$_6$): δ 13.00 (s, 1H, NH), 8.32 (s, 2H, NH$_2$), 2.42 (d, J=7.1 Hz, 2H, CH$_2$), 1.83-1.75 (m, 1H, CH), 1.69-1.59 (m, 4H, 2×CH$_2$), 1.26-1.09 (m, 4H, 2×CH$_2$), 1.02-0.91 (m, 2H, CH$_2$). $^{13}$C NMR (126 MHz, DMSO-d$_6$): δ 171.8, 164.6, 163.5, 42.8, 34.9, 32.7, 26.0, 25.8. APCI-MS: m/z 305.1 [M+H]⁺. HPLC retention time: 11.609 min. HPLC Purity: 100%.

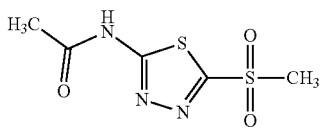

N-(5-(Methylsulfonyl)-1,3,4-thiadiazol-2-yl)acetamide (30, AB2-V-007). In a vial was added 5-(methylsulfonyl)-1,3,4-thiadiazol-2-amine (0.050 g, 1 eq., 0.28 mmol) followed by acetic anhydride (0.043 g, 1.5 eq., 0.42 mmol) in acetic acid (1 ml). The reaction mixture was stirred at 60° C. for 1 h. The solution was gradually cooled followed by the addition of water (10 ml). The suspension was cooled to 0° C. and the target compound was collected by filtration as a white solid (0.026 g, 0.12 mmol, 42%). $^1$H NMR (500 MHZ, DMSO-d$_6$): δ 13.26 (s, 1H, NH), 3.52 (s, 3H, CH$_3$), 2.27 (s, 3H, CH$_3$). $^{13}$C NMR (126 MHz, DMSO-d$_6$) δ 170.0, 162.7, 162.6, 43.6, 22.7. HPLC retention time: 11.118 min. HPLC Purity: 100%.

N-(4-sulfamoylphenyl)acetamide (31, Cao-XC-18). This molecule was purchased from a commercial vendor (Combi-Blocks, Cat #A59503) and characterized to ensure identity and purity. $^1$H NMR (500 MHZ, DMSO-d$_6$): δ 10.24 (s, 1H), 7.87-7.59 (m, 4H), 7.19 (s, 2H), 2.04 (s, 3H). $^{13}$C NMR (126 MHz, DMSO-d$_6$) δ 169.2, 142.5, 138.4, 127.0, 118.8, 24.4. APCI-MS: m/z 215.0 [M+H]⁺. HPLC retention time: 7.880 min. HPLC Purity: 97.5%.

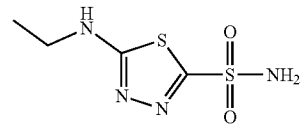

5-(ethylamino)-1,3,4-thiadiazole-2-sulfonamide (32, AG-103). Prepared according to procedure 1 using 2 (0.052 g, 0.29 mmol, 1.0 eq.), ethyl iodide (0.082 g, 0.35 mmol, 1.2 eq.), potassium carbonate (0.047 g, 0.35 mmol, 1.2 eq.) to produce 32 (0.003 g, 0.014 mmol, 41%). $^1$H NMR (500 MHZ, DMSO-d$_6$): δ 8.26 (s, 1H), 7.85 (s, 2H), 2.97 (q, J=7.2 Hz, 2H), 1.01 (t, J=7.2 Hz, 3H). $^{13}$C NMR (126 MHz, DMSO-d$_6$): δ 172.3, 153.2, 140.6, 129.1, 128.0 (q, J=31.5 Hz), 124.8 (q, J=3.9 Hz), 124.0 (q, J=272.2 Hz), 52.7. APCI-MS: m/z 208.9 [M+H]⁺. HPLC retention time: 8.416 min. HPLC Purity: 97.0%.

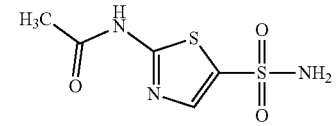

N-(5-sulfamoylthiazol-2-yl)acetamide (33, DF-304). This molecule was purchased from a commercial vendor (Enamine, Cat #EN300-79477) and characterized to ensure identity and purity. $^1$H NMR (500 MHZ, DMSO-d$_6$): δ 12.45 (s, 1H), 7.81 (s, 1H), 7.68 (s, 2H), 2.19 (s, 3H). $^{13}$C NMR (126 MHZ, DMSO-d$_6$) δ 169.3, 160.9, 140.4, 133.4, 22.4. APCI-MS: m/z 222.0 [M+H]⁺. HPLC retention time: 7.874 min. HPLC Purity: 97.6%.

2-morpholino-N-(5-sulfamoyl-1,3,4-thiadiazol-2-yl)acetamide (34, Cao1-XC-29). This molecule was synthesized via an alternative route described below in Scheme 2.

Scheme 2

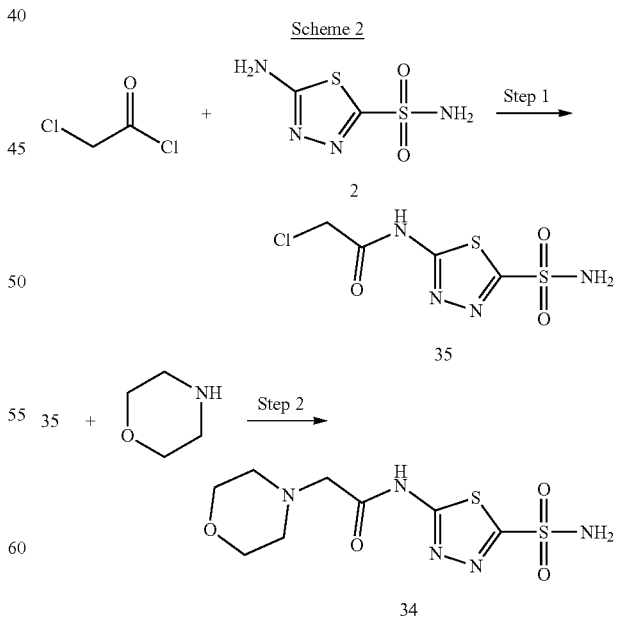

Step 1 (Cao1-XC-11 or Cao1-XC-26): To a vial was added the 2 (1.00 g, 5.55 mmol, 1 eq.) in anhydrous acetonitrile (25 mL) followed by addition of triethylamine (0.929 mL, 6.66 mmol, 1.2 eq.). The reaction was cooled to 0° C. then a solution of chloroacetyl chloride (0.485 mL, 6.10 mmol, 1.1 eq.) in acetonitrile (5 mL) was added over 15 minutes. The reaction was stirred at 0° C. for 6 hrs then allowed to warm to room temperature overnight. The solvent was removed in vacuo and the resulting crude material was treated with water (30 mL) and extracted with dichloromethane (3×40 mL). The organic layers were combined, washed with brine and dried over $MgSO_4$. The suspension was filtered and the filtrate was concentrated. The crude product was purified by column chromatography (30-50% EtOAc: Hex) to afford 35 as a white solid. $^1$H NMR (500 MHZ, DMSO-$d_6$): δ 13.37 (s, 1H), 8.33 (s, 2H), 4.48 (s, 2H). APCI-MS: m/z 256.9 [M+H]$^+$.

Step 2: To a vial was added intermediate 35 (0.050 g, 0.19 mmol, 1 eq.) and anhydrous THF (3 mL) and cooled to 0° C. This was followed by addition of triethylamine (0.054 mL, 0.39 mmol, 2.0 eq.) and morpholine (0.034 mL, 0.39 mmol, 2.0 eq.). The reaction stirred at 0° C. for 1 h then warmed to room temperature and stirred overnight. The reaction was then concentrated in vacuo and the crude product was adsorbed to Celite and purified by reverse-phase flash chromatography (5-100% acetonitrile: water) to afford 34 (0.049 g, 0.158 mmol, 82%) as an off-white solid. APCI-MS: m/z 308.0 [M+H]$^+$. HPLC retention time: 3.502 min. HPLC Purity: 97.9%.

In Vitro and In Vivo Evaluations

Feasibility in vivo study: AZM reduces VRE load in the intestines and faeces. The promising feature, and the specific and potent antimicrobial activity of CAIs, prompted us to evaluate the in vivo efficacy of AZM in our established mouse model of GI colonization by enterococci with features that mimic the antibiotic-induced enterococcal expansion observed in humans (Mohammad, H. et al., *Int J Antimicrob Agents* 2018, 51, 897-904; Abdelkhalek, A, et al., *PLoS One* 2018, 13, e0199710). We tested AZM (two clinical doses 10 and 20 mg/kg) in female 12-week-old C57BL/6 mice (n=5 mice per group) that were sensitized with ampicillin (0.5 g/mL in drinking water) for 7 days to reduce the microbiota present in the gastrointestinal tract and colonized with 108 CFU/mL of vancomycin-resistant *E. faecium*.

AZM exhibited a significant reduction in the feces (as early as 3rd day), cecal content and ileal content of infected mice after dosing once a day at 10 mg/kg or 20 mg/kg (clinical dose) compared to control mice (FIG. 1 Ileal data are shown). Remarkably, AZM outperformed linezolid, an antibiotic used clinically to treat VRE systemic infections. Although linezolid is used to treat VRE infections, it has not been proposed for use as a decolonizing agent. This is due, in part, to linezolid achieving a very low concentration in the stool of humans, and the propensity of linezolid to promote overgrowth of VRE when a high inoculum of bacteria (108 CFU) is present (Pultz, N. et al., *Antimicrob Agents Chemother* 2005, 49, 3513-3516). We thought that the rapid absorption of AZM from the gastrointestinal tract would limit their exposure time to VRE present in the gastrointestinal tract. In contrast, AZM remain in the gastrointestinal tract for a period of time, which appears to be sufficient to significantly decrease the burden of VRE present.

Figure 2:
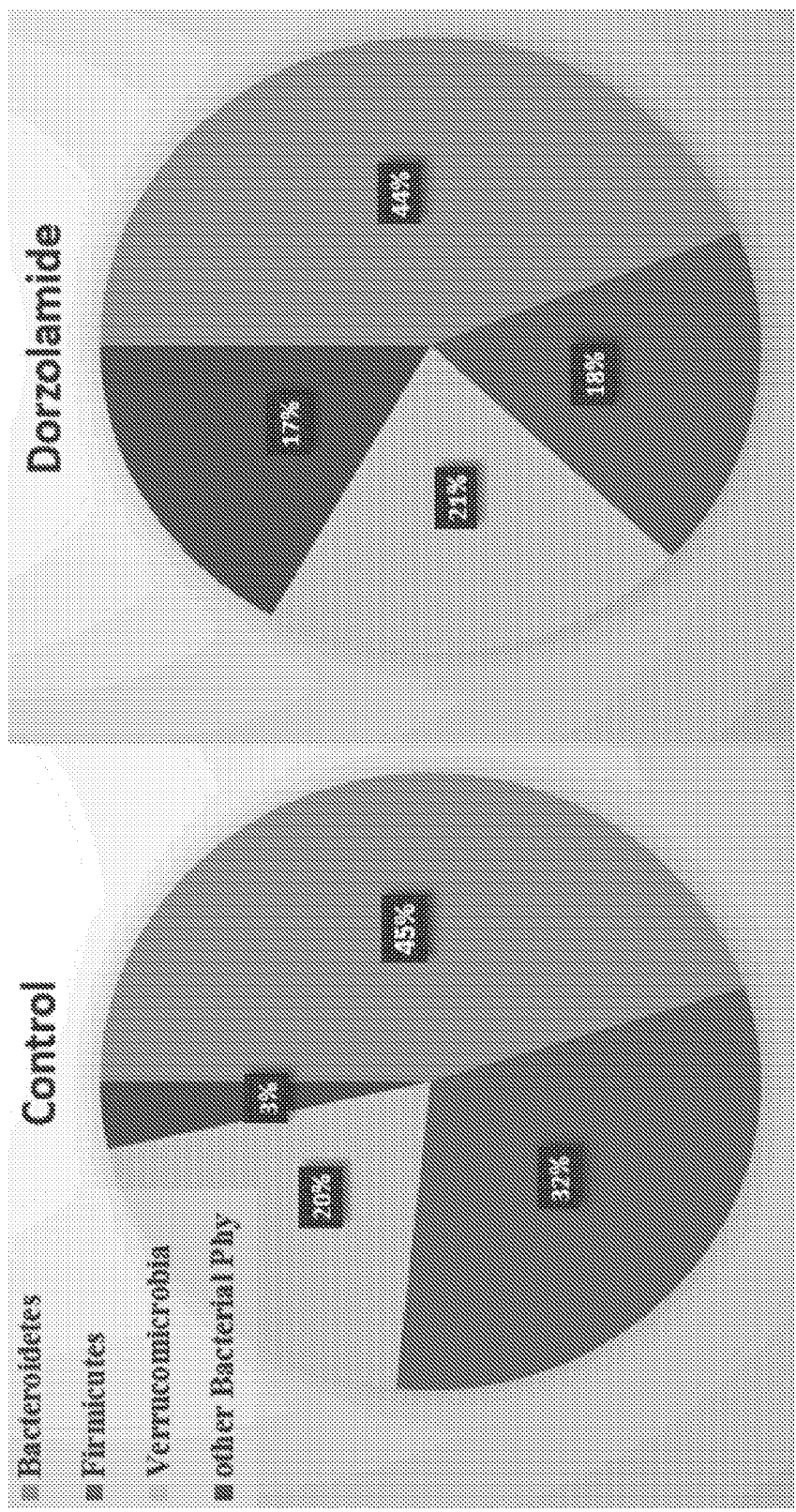
FIG. 2: Comparison of microbial community composition in the feces of treated mice. The pie charts show the distribution of the pooled tags recovered from each experimental group. Numbers are mean percentages of pooled tags in each experimental group assigned to particular phyla.

CAIs had no major impact on microbiota composition. An extremely promising and innovative feature of CAIs is their narrow spectrum of activity and their ability to decolonize VRE without harming the microbiome. A previous report investigating ramoplanin as a decolonizing agent against VRE found that ramoplanin altered the anaerobic microbiota present in the gastrointestinal tract (particularly affecting Gram-positive micro-organisms), which resulted in the overgrowth of resistant Gram-negative bacilli (namely *Klebsiella pneumoniae* and Enterobacteriaceae)$_2$. To characterize the impact of CAIs administration on the composition of the gut microbiota we performed the following assay6. Female 12-week-old $C_{57}BL/6$ mice (n=5 mice per group) were exposed to CAIs by oral gavage for 10 days (10 mg/kg daily). Twenty-four hours after last dose, mice were euthanized and cecal and colon contents were harvested. The microbiome was characterized using 16S rDNA gene sequencing. The microbiotas from treated mice were compared to those from a group of control mice. There was no major shift or change in taxonomic structure and composition of microbiota with CAIs treatment (FIG. 2 Dorzolamide data shown). However, at the phylum level, we observed decrease in Firmicutes in CAIs treatment groups and likely due to decrease of enterococci as *enterococcus* is a large genus of the phylum Firmicutes. The Verrucomicrobia and Bacteroidetes remain constant while other phyla increase to fill the remaining percentage from Firmicute loss. These data indicate that using CAIs and analogs may avoid side effects associated with traditional antibiotics and adverse events, particularly on the gut microbiota. Indeed, the use of traditional antibiotics can increase the selective pressure and contribute to the selection of other multi-drug-resistant organisms (Kofteridis D. et al., *Int J Infect Dis* 2009, 13, e313-315).

Figure 3A:
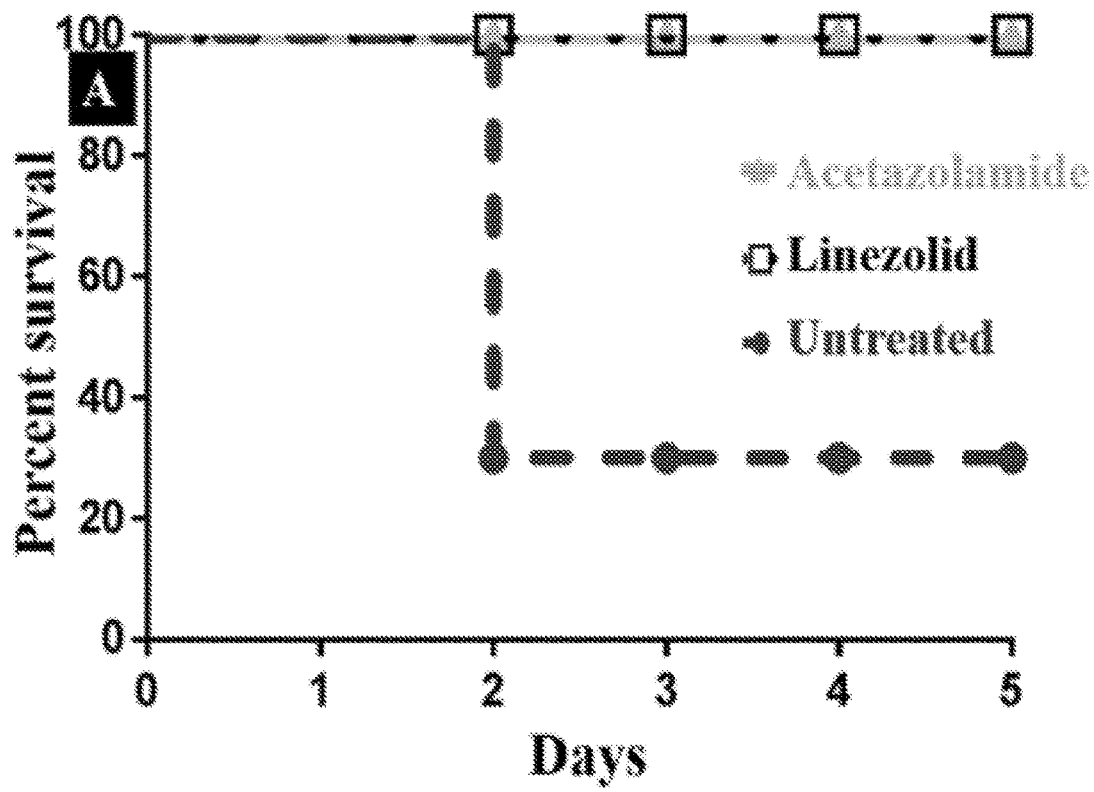
FIGS. 3A-3B show the efficacy of acetazolamide treatment of lethal VRE infection model. Percent survival (FIG. 3A), and bacterial load in the kidneys (FIG. 3B). (*) Significant from control and #significant from linezolid.
Figure 3B:
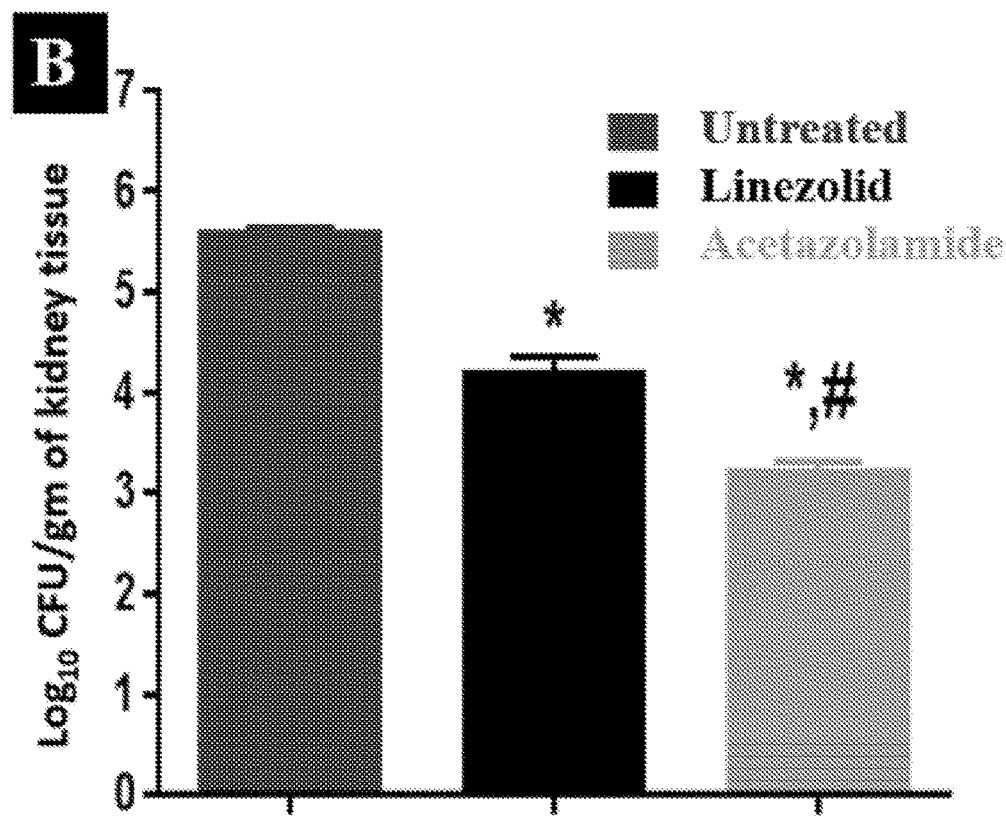

AZM is superior to linezolid in reducing the bacterial load in lethal VRE model. AZM is rapidly and almost completely absorbed from the GI tract (~100%) reaching peak plasma concentrations approximately 1-3 h after oral administration (Granero G E et al., *J Pharm Sci* 2008, 97, 3691-3699). (AZM serum concentration reaches 20-100 µg/mL after single oral dose. See Dahl, A. et al., *Stoke* 1995, 26, 2302-2306). We envisioned that standard dose 10-20 mg/kg should create enough plasma concentration above the MIC that should provide great advantage in the treatment of lethal VRE septicemic infections such as enterococcal peritonitis, an infection that has a high complication rate and it often treated with i.p. injections (Szeto, C C et al., *Kidney and Blood Pressure Research* 2017, 42, 837-843). To test this hypothesis, AZM and linezolid were evaluated systemically against VRE in a mouse peritonitis model (Arias, C A et al., *J Antimicrob Chemother* 2007, 60, 594-598). Briefly, groups (n=10) female 12 weeks old BALB/c mice were injected intraperitoneally with 50% lethal dose (LD50) VRE clinical isolate in 20% sterile rat fecal extract (4.7×107 CFU/mL of *E. faecium* NR 31909). Two hours after the bacterial challenge, mice received oral treatment with AZM or linezolid at 20 mg/kg daily for 4 days. Saline was used as a negative control. Mice were euthanized on day 5 and organs (liver, spleen and kidneys) were aseptically removed and homogenized, and viable VRE were enumerated by serial dilution and plating. Both AZM and linezolid protected 100% of the mice against a lethal dose of vancomycin-resistant strain of *E. faecalis* in the mouse peritonitis model (FIG. 3A). However, AZM was superior to linezolid in reducing the bacterial load in internal organs (Data for kidneys shown FIG. 3B).

AZM analogs are not toxic: While the PK for these new analogs yet to be defined, molecule 8 was scaled-up (~200 mg) and an in vivo efficacy and toxicity studies were performed. In this preliminary toxicity study C57BL/6 mice (n=5) were dosed 200 mg/kg twice daily (400 mg/kg daily) of AZM analog 8 for three days. None of the mice exhibited any signs of distress or toxicity and all the mice survived. Since oral LD50 (mouse) for (AZM) is very high (4300 mg/kg), we did not expect to see any sign of toxicity with the new analogs at the given dose.

Figure 4A:
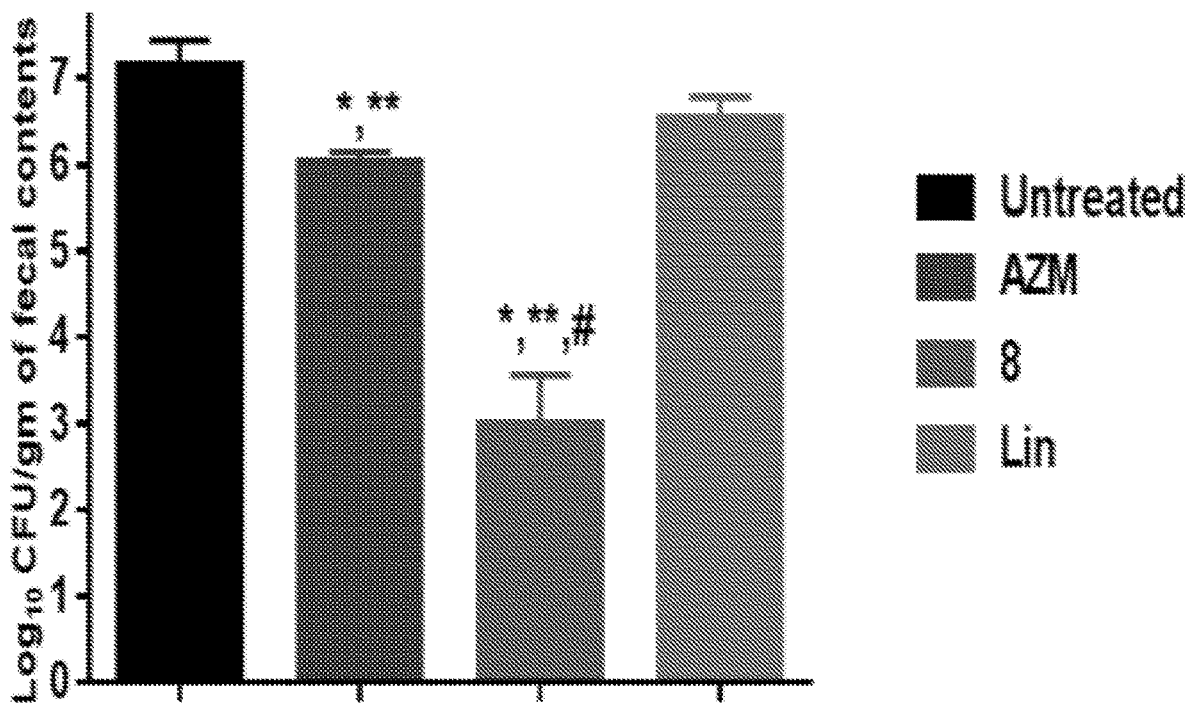
FIGS. 4A-4B show VRE in feces 3rd day (FIG. 4A) and Ileum (FIG. 4B) content of infected mice treated with drugs (10 mg/kg) once daily for 8 days. (*) significant from untreated, (**) significant from linezolid, (#) significant from AZM.
Figure 4B:
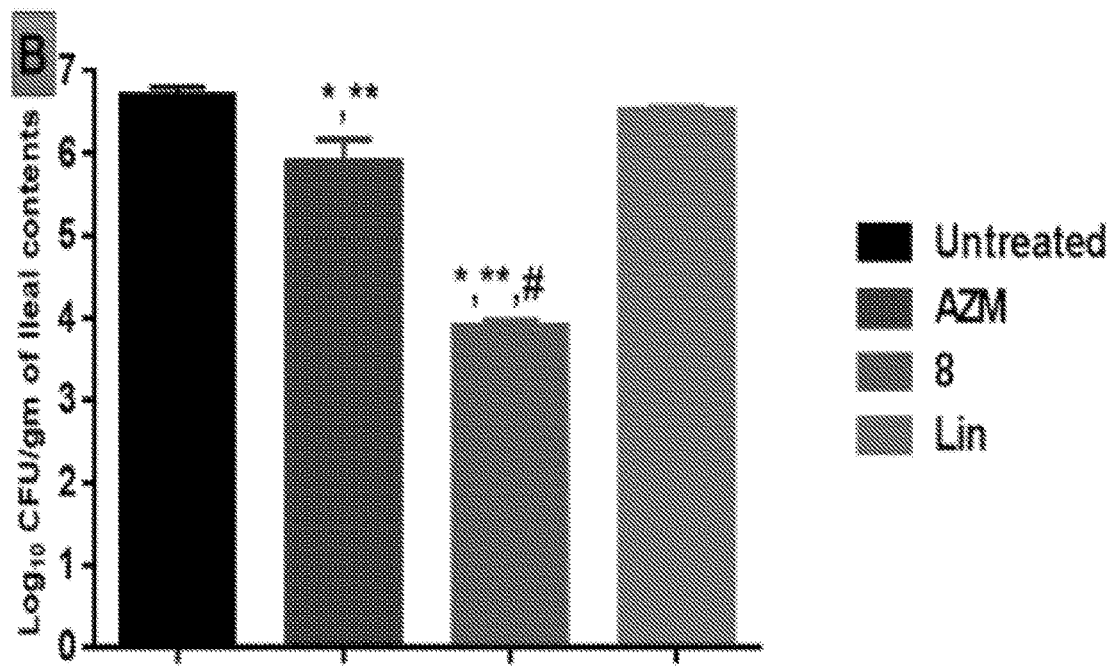

AZM analogs were superior to linezolid and AZM in reducing VRE in feces, caeca and ilea of infected mice. We tested AZM, analog 8 and linezolid in female 12-week-old C57BL/6 mice (n=5 mice per group) that were sensitized with ampicillin (0.5 g/mL in drinking water) for 7 days to reduce the microbiota present in the gastrointestinal tract and then colonized with 108 CFU/mL of vancomycin-resistant *E. faecium*. Mice were treated for 8 days with 10 mg/kg of drugs by oral gavage. Analog 8 was superior to AZM and linezolid in reducing VRE in the feces (as early as 3rd day), cecum, and ileum of infected mice (FIGS. 4A-4B).

MICs of Acetazolamide Analogues Against Vancomycin Resistant and Vancomycin Sensitive Enterococci The minimum inhibitory concentrations (MICs) of the compounds and control drugs were determined using the broth microdilution method, according to guidelines outlined by the Clinical and Laboratory Standards Institute (CLSI). Enterococci strains were grown aerobically overnight on tryptone soya agar plates at 37° C., afterwards a bacterial solution equivalent to 0.5 McFarland standard was prepared and diluted in tryptone soy broth (TSB) to achieve a bacterial concentration of about $5\times10^5$ CFU/mL and seeded in 96-well well plates. Compounds and control drugs were added in the first row of the 96-well plates and serially diluted along the plates. Plates were then incubated aerobically at 37° C. for 18-20 hours. MICs reported in Table 1 are the minimum concentration of the compounds/control drugs that could inhibit completely the visual growth of the bacteria. As presented in Table 1, Compounds AS005H, AS005J and AS004B exhibited the highest potent activity against the tested strains with MIC values ranging from 0.0625 to 1 µg/mL which exceeded the activity of acetacelamide that showed MIC values ranging from 2 to 4 µg/mL.

lined by the Clinical and Laboratory Standards Institute (CLSI) 1. Staphylococci strains were grown aerobically overnight on tryptone soya agar plates at 37° C., afterwards a bacterial solution equivalent to 0.5 McFarland standard was prepared and diluted in tryptone soy broth (TSB) to achieve a bacterial concentration of about $5\times10^5$ CFU/mL and seeded in 96-well well plates. Compounds and control drugs were added in the first row of the 96-well plates and serially diluted along the plates. Plates were then incubated aerobically at 37° C. for 18-20 hours. MICs reported in Table 2 are the minimum concentration of the compounds/control drugs that could inhibit completely the visual growth of the bacteria. Acetazolamide and its analogues did not exhibit antibacterial activity against the tested staphylococcal strains.

TABLE 2

MICs (µg/mL) of acetazolamide analogues against methicillin resistant *Staphylococcus aureus* (MRSA) and *Staphylococcus epidermidis*

| Compounds/Control Drugs | MRSA NRS 384 (MRSA USA300) | *Staphylococcus epidermidis* NRS 101 |
|---|---|---|
| 005D | >64 | >64 |
| 005B | >64 | >64 |
| AS004A | >64 | >64 |
| AS004B | >64 | >64 |
| AS005A | >64 | >64 |
| AS005H | >64 | >64 |
| AS005J | >64 | >64 |
| AS005K | >64 | >64 |
| Acetazolamide | >64 | >64 |
| Linezolid | 2 | ≤0.5 |
| Vancomycin | 1 | 4 |

TABLE 1

MICs (µg/mL) of acetazolamide analogues against vancomycin resistant and vancomycin sensitive *Enterococci* using Tryptone soy broth (TSB)

| Compounds/Control Drugs (These are the Lot#'s in the Master Data File) | *Enterococcus fecalis* Strain MMH594-NR31975 | *Enterococcus faecium* Patient #2-1-NR-31909 | *Enterococcus faecium* Patient #3-1 NR-31912 | *Enterococcus fecalis* Strain SF 28073-NR31972 | *Enterococcus fecalis* Strain SF24413 NR31971 | *Enterococcus fecalis* Strain SF 24397 NR31970 | *Enterococcus faecalis*—S613 HM-334 | *Enterococcus faecium* E417-HM-965 |
|---|---|---|---|---|---|---|---|---|
| 005D | 1 | 0.5 | 1 | 2 | 1 | 1 | 1 | 0.5 |
| 005B | 4 | 1 | 1 | 8 | 4 | 4 | 4 | 2 |
| AS004A | 2 | 1 | 1 | 4 | 4 | 4 | 2 | 1 |
| AS004B | 1 | 0.5 | 1 | 0.5 | 0.5 | 0.5 | 0.5 | 0.5 |
| AS005A | 2 | 1 | 1 | 2 | 2 | 2 | 2 | 1 |
| AS005H | 0.06 | 0.125 | 1 | 0.125 | 0.06 | 0.125 | 0.125 | 0.25 |
| AS005J | 0.5 | 0.5 | 1 | 0.5 | 0.5 | 0.5 | 0.5 | 0.25 |
| AS005K | 1 | 0.25 | 1 | 1 | 1 | 1 | 1 | 0.25 |
| Acetazolamide | 4 | 2 | 2 | 4 | 4 | 2 | 2 | 2 |
| Linezolid | 1 | 1 | 1 | 1 | 1 | 1 | 1 | 1 |
| Vancomycin | 2 | >64 | >64 | >64 | 32 | 2 | >64 | >64 |

Screening of Acetazolamide Analogues Against Staphylococci Strains

Next, those compounds were further screened against some other Gram positive bacteria to assess their anti VRE activity and to confirm their selective activity against VRE (Table 2).

The minimum inhibitory concentrations (MICs) of the compounds and control drugs were determined using the broth microdilution method, according to guidelines out- Screening of Acetazolamide Analogues Against Human Gut Microbiota Three different bacterial strains were used in this experiment; *Bifidobacterium* (anaerobic Gram positive bacteria), *Bacteroides* (anaerobic Gram negative bacteria) and *Lactobacillus* (microaerophilic Gram positive bacteria). *Bifidobacterium* and *Bacteroides* were first grown for 48 hours at 37° C., anaerobically using brain heart infusion supplemented (BHIS) agar (Brain heart infusion agar supplemented with hemin, vitamin K and L-cysteine). *Lactobacillus* was cultivated on MRS agar and incubated in presence of 5% CO2 for 48 hours at 37° C. Each bacterium was suspended in phosphate buffered saline (PBS) to produce a suspension with optical density that matches 0.5 McFarland standard and diluted in brain heart infusion supplemented broth (for *Bifidobacterium* and *Bacteroides*) or in MRS broth (for *Lactobacillus*) to achieve bacterial concentration of approximately $5 \times 10^5$ CFU/ml. Bacteria were then seeded in 96-well plates containing serial dilutions of the compounds and incubated as mentioned previously for 48 hours. MICs reported in Table 3 are the minimum concentrations of the compounds/control drugs that could completely inhibit the visual growth of the bacteria. Acetazolamide and its analogues did not inhibit the tested human gut microbiota which adds is advantageous for these compounds to be used in treating VRE infections without disturbing the human gut microbiota.

In Vitro Cytotoxicity Analysis of Acetazolamide Analogues Against VERO Cells

Toxicity assessment: Compounds AS005H, AS005J, AS004B, AS005K, AS005A and 005D were assayed (at concentrations of 64 and 128 μg/mL) against a fibroblast-like monkey kidney cell line (VERO cell) to determine the potential toxic effect in vitro. Briefly, cells were cultured in Minimum Essential Medium (MEM) supplemented with 10% fetal bovine serum (FBS), 1 mM sodium pyruvate, and penicillin-streptomycin at 37° C. with CO2 (5%). Control cells received DMSO alone at a concentration equal to that in drug-treated cell samples. The cells were incubated with the compounds (in triplicate) in a 96-well plate at 37° C. with CO2 (5%) for two hours. The assay reagent MTS 3-(4,5-dimethylthiazol-2-yl)-5-(3-carboxymethoxyphenyl)-2-(4-sulfophenyl)-2H-tetrazolium) (Promega, Madison, WI, USA) was subsequently added and the plate was incubated for four hours. Absorbance readings (at $OD_{490}$) were taken

TABLE 3

MICs (μg/mL) of acetazolamide analogues against human normal gut microbiota

| Compounds/ Control Drugs | *Bifidobacterium longum* subsp. *Longum*—44B HM 845 | *Bifidobacterium breve*— JCP7499 HIM 1120 | *Bacteroides fragilis*— CL07T00C 01 HIM-709 | *Bacteroides dorei*— CL02T12C 06 HM-719 | *Lactobacillus casei* ATCC 334 | *Lactobacillus gasseri* EX336960VC 03 HIM-400 |
|---|---|---|---|---|---|---|
| 005D | >64 | >64 | >64 | >64 | >64 | >64 |
| 005B | >64 | >64 | >64 | >64 | >64 | >64 |
| AS004A | >64 | >64 | >64 | >64 | >64 | >64 |
| AS004B | >64 | >64 | >64 | >64 | >64 | >64 |
| AS005A | >64 | >64 | >64 | >64 | >64 | >64 |
| AS005H | >64 | >64 | >64 | >64 | >64 | >64 |
| AS005J | >64 | >64 | >64 | >64 | >64 | >64 |
| AS005K | >64 | >64 | >64 | >64 | >64 | >64 |
| Acetazolamide | >64 | >64 | >64 | >64 | >64 | >64 |
| Linezolid | ≤0.5 | ≤0.5 | 2 | 1 | 1 | 2 |
| Vancomycin | 8 | 8 | 64 | 64 | >64 | >64 |

MICs of the Most Active Compounds Against Acetazolamide-Resistant Mutant Strains of VRE Then, The most active analogues were further screened against some mutant strains of *Enterococcus fecalis* Strain MMH594 NR 31975 which are acetazolamide-resistant. Results are shown in Table 4. In general, acetazolamide analogues exhibited higher antibacterial activity against the tested mutant strains than acetazolamide. Compound AS005H exhibited the highest activity against the acetazolamide-resistant mutant strains of *E. fecalis* NR 31975 with MIC values ranging from 0.0625 to 2 μg/mL.

using a kinetic microplate reader (Molecular Devices, Sunnyvale, CA, USA). The quantity of viable cells after treatment with each compound was expressed as a percentage of the viability of DMSO-treated control cells (average of triplicate wells±standard deviation). The toxicity data was analyzed via a two-way ANOVA, with post hoc Dunnet's multiple comparisons test (P<0.05), utilizing GraphPad Prism 6.0 (GraphPad Software, La Jolla, CA).

Figure 5:
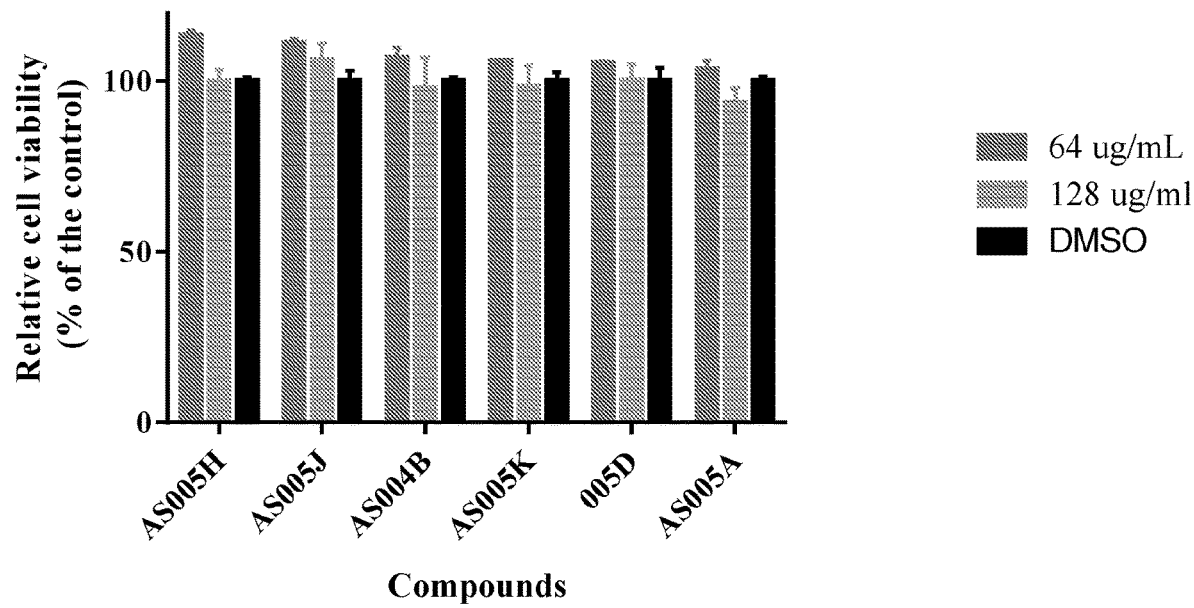
FIG. 5 shows toxicity analysis of acetazolamide analogues against fibroblast-like monkey kidney cell line (VERO cell). Percent viable mammalian cells (measured as average absorbance ratio (test agent relative to DMSO) for cytotoxicity analysis of compounds AS005H, AS005J, AS004B, AS005K, AS005A and 005D (tested in triplicates) at 64 and 128 μg/mL against VERO cells using the MTS 3-(4,5-dimethylthiazol-2-yl)-5-(3-carboxymethoxyphenyl)-2-(4-sulfophenyl)-2H-tetrazolium) assay. Dimethyl sulfoxide (DMSO) was used as a negative control to determine a baseline measurement for the cytotoxic impact of each compound. The absorbance values represent an average of a minimum of three samples analyzed for each compound. Error bars represent standard deviation values for the absorbance values. A two-way ANOVA, with post hoc Dunnet's multiple comparisons test, determined statistical difference between the values obtained for each compound and DMSO (denoted by the asterisk) ($P<0.05$). All the tested compounds were non-toxic to VERO cells at concentration up to 128 μg/mL.

FIG. 5 shows toxicity analysis of acetazolamide analogues against fibroblast-like monkey kidney cell line (VERO cell).

TABLE 4

MICs (μg/mL) of the active acetazolamide analogues against mutant strains of *Enterococcus fecalis* NR 31975

| Compounds/ Control Drugs | Mutant-2 | Mutant-3 | Mutant-4 | Mutant-5 | Mutant-6 | Mutant-7 | Mutant-8 | Mutant-9 | Mutant-11 | Mutant-12 | Mutant-13 | Mutant-14 | Mutant-15 | Wild-type *E. fecalis* |
|---|---|---|---|---|---|---|---|---|---|---|---|---|---|---|
| AS005H | 2 | 1 | 1 | 1 | 1 | 0.25 | 2 | 1 | 2 | 2 | 1 | 1 | 1 | 0.0625 |
| AS005J | 8 | 4 | 8 | 4 | 16 | 4 | 4 | 4 | 4 | 8 | 4 | 4 | 8 | 1 |
| AS004B | 8 | 4 | 8 | 4 | 16 | 4 | 8 | 8 | 4 | 8 | 4 | 4 | 4 | 0.5 |
| AS005K | 8 | 8 | 16 | 8 | 8 | 8 | 8 | 16 | 8 | 16 | 16 | 8 | 16 | 2 |
| 005D | 8 | 16 | 16 | 16 | 8 | 8 | 16 | 8 | 8 | 8 | 16 | 8 | 16 | 2 |
| Acetazolamide | 16 | 32 | 32 | 32 | 32 | 16 | 32 | 16 | 16 | 32 | 32 | 32 | 32 | 2 |
| Linezolid | 4 | 4 | 4 | 4 | 4 | 2 | 8 | 4 | 4 | 4 | 4 | 4 | 8 | 1 |

Percent viable mammalian cells (measured as average absorbance ratio (test agent relative to DMSO) for cytotoxicity analysis of compounds AS005H, AS005J, AS004B, AS005K, AS005A and 005D (tested in triplicates) at 64 and 128 µg/mL against VERO cells using the MTS 3-(4,5-dimethylthiazol-2-yl)-5-(3-carboxymethoxyphenyl)-2-(4-sulfophenyl)-2H-tetrazolium) assay. Dimethyl sulfoxide (DMSO) was used as a negative control to determine a baseline measurement for the cytotoxic impact of each compound. The absorbance values represent an average of a minimum of three samples analyzed for each compound. Error bars represent standard deviation values for the absorbance values. A two-way ANOVA, with post hoc Dunnet's multiple comparisons test, determined statistical difference between the values obtained for each compound and DMSO (denoted by the asterisk) (P<0.05). All the tested compounds were non-toxic to VERO cells at concentration up to 128 µg/mL.

In Vitro Cytotoxicity Analysis of Acetazolamide Analogues Against Caco-2 Cells

Method: Compounds AS005H, AS005J, AS004B, AS005K, AS005A and 005D were assayed (at concentrations of 64 and 128 µg/mL) against a human colorectal adenocarcinoma (Caco-2) cell to determine the potential toxic effect to mammalian cells in vitro. Briefly, cells were cultured in Dulbecco's Modified Eagle Medium (DMEM) supplemented with 20% fetal bovine serum (FBS), non-essential amino acids (1×), penicillin-streptomycin at 37° C. with CO2 (5%). Control cells received DMSO alone at a concentration equal to that in drug-treated cell samples. The cells were incubated with the compounds (in triplicate) in a 96-well plate at 37° C. with CO2 (5%) for two hours. The assay reagent MTS 3-(4,5-dimethylthiazol-2-yl)-5-(3-carboxymethoxyphenyl)-2-(4-sulfophenyl)-2H-tetrazolium) (Promega, Madison, WI, USA) was subsequently added and the plate was incubated for four hours. Absorbance readings (at $OD_{490}$) were taken using a kinetic microplate reader (Molecular Devices, Sunnyvale, CA, USA). The quantity of viable cells after treatment with each compound was expressed as a percentage of the viability of DMSO-treated control cells (average of triplicate wells±standard deviation). The toxicity data was analyzed via a two-way ANOVA, with post hoc Dunnet's multiple comparisons test (P<0.05), utilizing GraphPad Prism 6.0 (GraphPad Software, La Jolla, CA).

Figure 6:
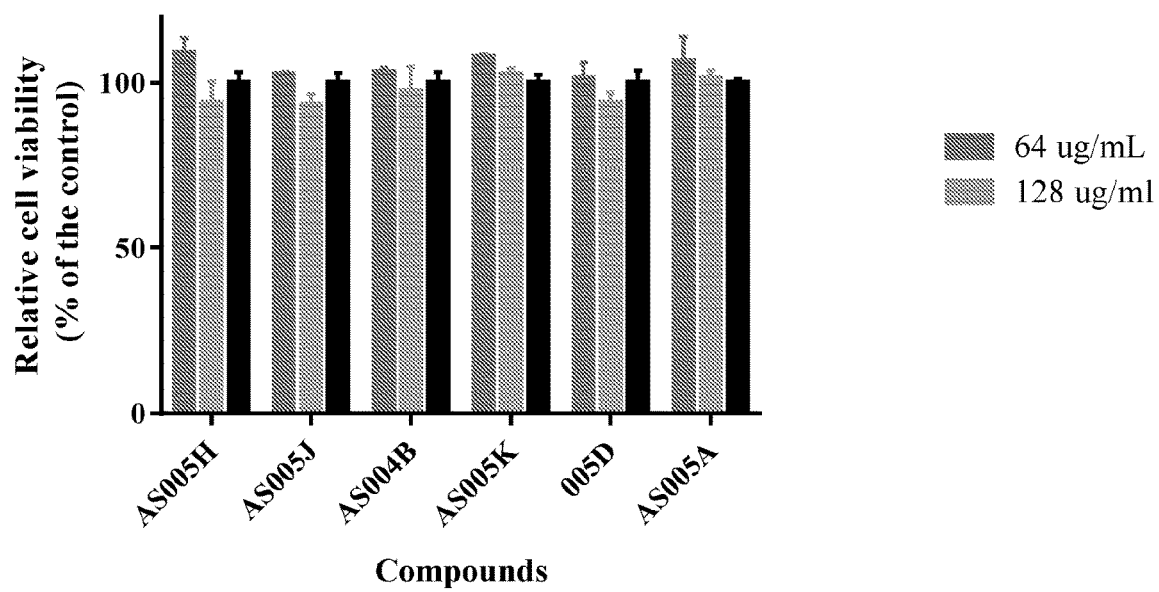
FIG. 6 shows toxicity analysis of acetazolamide analogues against human colorectal cells (Caco-2). Percent viable mammalian cells (measured as average absorbance ratio (test agent relative to DMSO) for cytotoxicity analysis of AS005H, AS005J, AS004B, AS005K, AS005A and 005D compounds (tested in triplicate) at 64 and 128 μg/mL against Caco-2 cells using the MTS 3-(4,5-dimethylthiazol-2-yl)-5-(3-carboxymethoxyphenyl)-2-(4-sulfophenyl)-2H-tetrazolium) assay. Dimethyl sulfoxide (DMSO) was used as a negative control to determine a baseline measurement for the cytotoxic impact of each compound. The absorbance values represent an average of a minimum of three samples analyzed for each compound. Error bars represent standard deviation values for the absorbance values. A two-way ANOVA, with post hoc Dunnet's multiple comparisons test, determined statistical difference (denoted by the asterisk) ($P<0.05$) between the values obtained for each compound and DMSO (negative control, used as solvent for the compounds). All the tested compounds were non-toxic to Caco-2 cells at concentration up to 128 μg/mL.

FIG. 6 shows toxicity analysis of acetazolamide analogues against human colorectal cells (Caco-2). Percent viable mammalian cells (measured as average absorbance ratio (test agent relative to DMSO) for cytotoxicity analysis of AS005H, AS005J, AS004B, AS005K, AS005A and 005D compounds (tested in triplicate) at 64 and 128 µg/mL against Caco-2 cells using the MTS 3-(4,5-dimethylthiazol-2-yl)-5-(3-carboxymethoxyphenyl)-2-(4-sulfophenyl)-2H-tetrazolium) assay. Dimethyl sulfoxide (DMSO) was used as a negative control to determine a baseline measurement for the cytotoxic impact of each compound. The absorbance values represent an average of a minimum of three samples analyzed for each compound. Error bars represent standard deviation values for the absorbance values. A two-way ANOVA, with post hoc Dunnet's multiple comparisons test, determined statistical difference (denoted by the asterisk) (P<0.05) between the values obtained for each compound and DMSO (negative control, used as solvent for the compounds). All the tested compounds were non-toxic to Caco-2 cells at concentration up to 128 µg/mL.

MICs of Carbonic Anhydrase Inhibitors (CAIs) Against Vancomycin Sensitive and Vancomycin Resistant Enterococci:

The minimum inhibitory concentrations (MICs) of CAIs were tested against clinical isolates of vancomycin sensitive and vancomycin resistant Enterococci strains as per the guidelines provided by the Clinical and Laboratory Standards Institute (CLSI). The selected strains of Enterococci were streaked on Tryptic Soy Agar (TSA) plates and let grow for 24 hours at 37° C. Afterwards, a bacterial solution equivalent to 0.5 McFarland standard was prepared and diluted in tryptone soy broth (TSB) or brain heart infusion broth (BHIB) to achieve a bacterial concentration of about $5 \times 10^5$ CFU/mL and seeded in 96-well well plates. Compounds and control drugs were added in the first row of the 96-well plates and serially diluted along the plates. Plates were then incubated aerobically at 37° C. for 18-20 hours. MICs reported in Table 5 are the minimum concentration of the compounds/control drugs that could inhibit completely the visual growth of the bacteria. The MIC values of CAIs against the tested VRE strains were higher in BHIB than in TSB. This may be due to binding of these drugs to proteins. Thus, they are almost inactive in BHIB and showed potent activity in TSB. Acetazolamide, brinzolamide, ethoxzolamide and methazolamide exhibited higher anti-VRE activity against other drugs. They inhibited the VRE strains at MIC values ranging from 1 to 4 µg/mL.

TABLE 5

MICs (µg/mL) of CAIs against vancomycin sensitive and vancomycin resistant *Enterococci* using brain heart infusion broth (BHIB) and tryptone soya broth (TSB)

| | *Enterococcus fecalis* Strain SF 24397 NR31970 | | *Enterococcus faecium* Patient #2-1-NR-31909 | | *Enterococcus faecium* E417-HM-965 | | *Enterococcus faecalis*—S613 HM-334 | |
|---|---|---|---|---|---|---|---|---|
| | BHIB | TSB | BHIB | TSB | BHIB | TSB | BHIIB | TSB |
| Acetazolamide | >128 | 2 | 64 | 2 | 8 | 2 | >128 | 2 |
| Brinzolamide | >128 | 2 | >128 | 4 | 16 | 2 | >128 | 2 |
| Dichlophenamide | >128 | 16 | >128 | 2 | 16 | 1 | >128 | 16 |
| Dorzolamide | >128 | 8 | >128 | 8 | 128 | 16 | >128 | 8 |
| Ethoxzolamide | >128 | 2 | 64 | 2 | 16 | 2 | >128 | 1 |
| Methazolamide | >128 | 2 | >128 | 8 | 64 | 4 | >128 | 1 |
| Linezolid | 1 | 1 | 1 | 1 | 1 | 1 | 1 | 1 |
| Vancomycin | 2 | 2 | >128 | >128 | >128 | >128 | >128 | >128 |
| Daptomycin | 2 | 1 | 16 | 8 | 16 | 4 | 2 | 1 |

MICs (μg/mL) of carbonic anhydrase inhibitors (CAIs) and the most potent acetazolamide analogues against *Enterococcus faecalis*—S613 HM 334 in presence of 4% human serum albumin (HAS)

The minimum inhibitory concentrations (MICs) of CAIs were tested against vancomycin resistant *Enterococcus faecalis*—S613 HM 334 strain as per the guidelines provided by the Clinical and Laboratory Standards Institute (CLSI). The selected strain was streaked on Tryptic Soy Agar (TSA) plate and let grow for 24 hours at 37° C. Afterwards, a bacterial solution equivalent to 0.5 McFarland standard was prepared and diluted in tryptone soy broth (TSB) supplemented with 4% human serum albumin (HAS) to achieve a bacterial concentration of about $5 \times 10^5$ CFU/mL and seeded in 96-well well plates. Compounds and control drugs were added in the first row of the 96-well plates and serially diluted along the plates. Plates were then incubated aerobically at 37° C. for 18-20 hours. MICs reported in table (6) are the minimum concentration of the compounds/control drugs that could inhibit completely the visual growth of the bacteria. As shown in Table 6, all CAIs and Acetazolamide analogues showed higher binding to human serm albumin.

TABLE 6

MICs (μg/mL) of CAIs and the most potent acetazolamide analogues against *Enterococcus faecalis*-S613 HM 334 in presence of 4% human serum albumin

|  | *Enterococcus faecalis*-S613 HM-334 |
|---|---|
| Acetazolamide | >256 |
| Brinzolamide | >256 |
| Dichlophenamide | >256 |
| Dorzolamide | >256 |
| Ethoxzolamide | >256 |
| Methazolamide | >256 |
| AS004B | >256 |
| AS005H | >256 |
| AS005J | >256 |
| Daptomycin | 16 |

TABLE 7

Antibacterial activities of selected compounds minimal inhibition concentration (MICs) in TSB (μg/mL)

| Compound ID | Lot# | E. faecalis MMH594-NR31975 | E faecium Patient #2 | E faecium Patient #3 | E. faecalis SF 28073-NR31972 | E. faecalis SF24413 NR31971 | E faecalis SF 24397 NR31970 | E. faecalis S613 HM-334 | E. faecium E417-HM-965 |
|---|---|---|---|---|---|---|---|---|---|
| Linezolid | | 1 | 1 | 1 | 1 | 1 | 1 | 1 | 1 |
| Vancomycin | | 2 | >64 | >64 | >64 | 32 | 2 | >64 | >64 |
| Acetozolamide | | 4 | 2 | 2 | 4 | 4 | 2 | 2 | 2 |
| CAI0001 | AT3-006-2-3 | | 8 | >64 | >64 | | | | >64 |
| CAI0002 | AT3-009 | | >64 | >64 | >64 | | | | >64 |
| CAI0003 | AT3-010 | | >64 | >64 | >64 | | | | >64 |
| CAI0004 | AT3-011 | | 8 | 8 | 8 | | | | 16 |
| CAI0005 | AT3-013 | | >64 | | >64 | | | | >64 |
| CAI0006 | AT3-014 | | >64 | | >64 | | | | >64 |
| CAI0007 | AT3-015 | | 8 | 8 | 4 | | | | 8 |
| CAI0008 | AT3-016 | | >64 | >64 | >64 | | | | >64 |
| CAI0009 | AS-004A | 2 | 1 | 1 | 4 | 4 | 4 | 2 | 1 |
| CAI0010 | AS-004B | 0.25 | 0.125 | 0.25 | 0.5 | 0.25 | 0.25 | 0.125 | 0.25 |
| CAI0011 | AS-005A | 2 | 1 | 1 | 2 | 2 | 2 | 2 | 1 |
| CAI0012 | AS-005B | 4 | 1 | 1 | 8 | 4 | 4 | 4 | 2 |
| CAI0013 | AS-005D | 1 | 0.5 | 1 | 2 | 1 | 1 | 1 | 0.5 |
| CAI0014 | AS-005E | | | | | | | | |
| CAI0015 | AS-005H | 0.06 | 0.06 | 0.125 | 0.06 | 0.06 | 0.06 | 0.06 | 0.06 |
| CAI0016 | AS-005J | 0.25 | 0.25 | 0.5 | 0.5 | 0.5 | 0.25 | 0.25 | |
| CAI0017 | AS-005K | 1 | 0.25 | 1 | 1 | 1 | 1 | 1 | 0.25 |
| CAI0018 | JK-VRE-001-1 | 0.5 | 0.25 | 0.5 | 1 | 1 | 1 | 1 | 0.5 |
| CAI0019 | JK5-VRE-004 | 0.015 | 0.003 | 0.007 | 0.015 | 0.015 | 0.015 | 0.007 | 0.007 |
| CAI0020 | JK5-VRE-005 | 0.007 | 0.001 | 0.007 | 0.003 | 0.015 | 0.015 | 0.007 | 0.007 |
| CAI0021 | JK5-VRE-006 | 0.03 | 0.003 | 0.03 | 0.03 | 0.06 | 0.03 | 0.03 | 0.06 |
| CAI0022 | AB2-VRE-001 | 0.25 | 0.015 | 0.125 | 0.25 | 0.5 | 0.25 | 0.25 | 0.25 |
| CAI0023 | AB2-VRE-002 | 0.5 | 0.06 | 0.25 | 1 | 0.5 | 0.5 | 0.5 | 0.25 |
| CAI0024 | AB2-VRE-004 | 0.25 | 0.015 | 0.125 | 0.25 | 0.25 | 0.25 | 0.25 | 0.25 |
| CAI0025 | AB2-VRE-007 | >128 | >128 | >128 | >128 | >128 | >128 | >128 | >128 |
| CAI0026 | AS-005M | 0.25 | 0.003 | 0.125 | 0.5 | 0.25 | 0.25 | 0.25 | 0.125 |
| CAI0027 | AS-005N | 0.015 | 0.001 | 0.007 | 0.015 | 0.015 | 0.007 | 0.007 | 0.015 |
| CAI0028 | AS-005L | 0.03 | 0.003 | 0.003 | 0.03 | 0.03 | 0.015 | 0.03 | 0.015 |
| CAI0029 | AS-005W | 0.015 | 0.001 | 0.03 | 0.015 | 0.03 | 0.007 | 0.015 | 0.06 |

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

It is intended that that the scope of the present methods and compositions be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

What is claimed is:

1. A method for treating a patient with a bacterial infection comprising the step of administrating a therapeutically effective amount of a carbonic anhydrase inhibitor having the formula (I), or a pharmaceutically acceptable salt thereof, together with one or more diluents, excipients or carriers, to the patient in need of treatment for said infection,

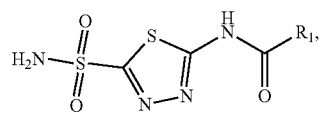

(I)

wherein
$R_1$ is

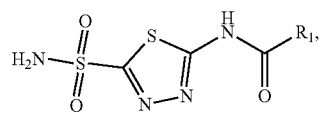

or
an alkynyl, each of which is optionally substituted.

2. A method for decolonizing a patient with a bacterial infection comprising the step of administrating a therapeutically effective amount of a carbonic anhydrase inhibitor having the formula (I), or a pharmaceutically acceptable salt thereof, together with one or more diluents, excipients or carriers, to the patient in need of treatment,

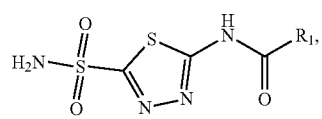

(I)

wherein
$R_1$ is

or
an alkynyl, each of which is optionally substituted.

3. The method of claim 1, wherein said carbonic anhydrase inhibitor is

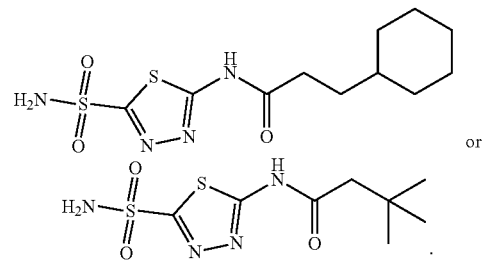

or

4. The method of claim 1, wherein said bacterial infection is an infection caused by a vancomycin-resistant or vancomycin susceptible bacteria.

5. The method of claim 4, wherein said bacteria is an *Enterococcus* species.

6. The method of claim 5, wherein said *Enterococcus* species comprises *Enterococcus faecium, Enterococcus faecalis, Enterococcus gallinarum, Enterococcus casseliflavus, Enterococcus durans, Enterococcus hirae, Enterococcus saccharolyticus*, and *Enterococcus raffinosus*.

7. A compound having the formula (I)

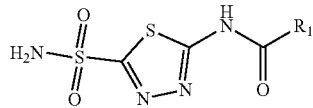

(I)

or a pharmaceutically acceptable salt thereof, wherein
$R_1$ is

or
an alkynyl, each of which is optionally substituted.

8. The compound of claim 7, wherein said compound is

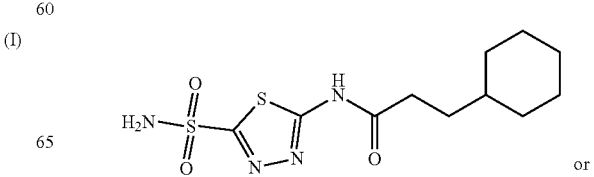

or

-continued

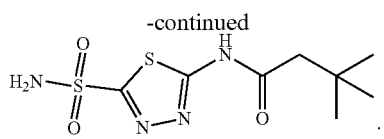

9. A pharmaceutical composition comprising one or more compounds of formula (I) according to claim 7, or a pharmaceutically acceptable salt thereof, together with one or more diluents, excipients or carriers.

10. A pharmaceutical composition comprising one or more compounds of claim 8, or a pharmaceutically acceptable salt thereof, together with one or more diluents, excipients or carriers, for use as a medicament.

11. The method of claim 1, wherein said compound is

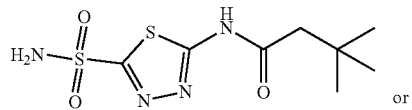 or

-continued

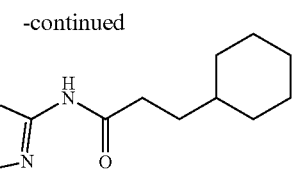

12. The method of claim 2, wherein said compound is

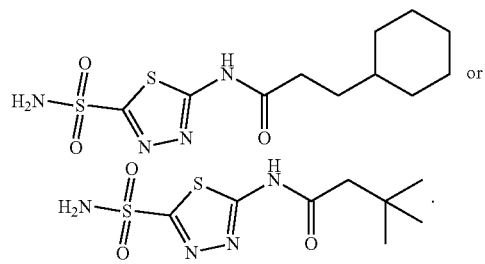

\* \* \* \* \*